US010632099B2

(12) United States Patent
Croatt et al.

(10) Patent No.: US 10,632,099 B2
(45) Date of Patent: Apr. 28, 2020

(54) NON-AROMATIC DIFLUORO ANALOGUES OF RESORCYLIC ACID LACTONES

(71) Applicants: The University of North Carolina at Greensboro, Greensboro, NC (US); Cedric Pearce, Chapel Hill, NC (US)

(72) Inventors: Mitchell P. Croatt, Greensboro, NC (US); Lara Fakhouri, Greensboro, NC (US); Nicholas H. Oberlies, Greensboro, NC (US); Cedric Pearce, Chapel Hill, NC (US)

(73) Assignee: University of North Carolina at Greensboro, Greensboro, NC (US)

( * ) Notice: Subject to any disclaimer, the term of this patent is extended or adjusted under 35 U.S.C. 154(b) by 0 days.

(21) Appl. No.: 16/556,626

(22) Filed: Aug. 30, 2019

(65) Prior Publication Data
US 2019/0381002 A1 Dec. 19, 2019

Related U.S. Application Data

(62) Division of application No. 15/579,251, filed as application No. PCT/US2016/034562 on May 27, 2016, now Pat. No. 10,434,085.

(60) Provisional application No. 62/170,789, filed on Jun. 4, 2015.

(51) Int. Cl.
A61K 31/365 (2006.01)
C07D 313/00 (2006.01)
C07D 493/04 (2006.01)
A61P 35/02 (2006.01)
A61K 31/336 (2006.01)

(52) U.S. Cl.
CPC .......... *A61K 31/365* (2013.01); *A61K 31/336* (2013.01); *A61P 35/02* (2018.01); *C07D 313/00* (2013.01); *C07D 493/04* (2013.01)

(58) Field of Classification Search
CPC .................................................. C07D 493/04
See application file for complete search history.

(56) References Cited

U.S. PATENT DOCUMENTS

| 4,239,772 | A | 12/1980 | Shipchandler |
| 4,336,243 | A | 6/1982 | Sanvordeker et al. |
| 5,728,726 | A | 3/1998 | Giese et al. |
| 5,977,165 | A | 11/1999 | Agatsuma et al. |
| 7,115,651 | B2 | 10/2006 | Danishefsky et al. |
| 7,799,827 | B2 | 9/2010 | Boivin et al. |
| 7,915,306 | B2 | 3/2011 | Chiba et al. |
| 8,067,412 | B2 | 11/2011 | Winssinger et al. |
| 8,329,742 | B2 | 12/2012 | Boivin et al. |
| 8,450,305 | B2 | 5/2013 | Winssinger et al. |
| 8,513,440 | B2 | 8/2013 | Winssinger et al. |
| 8,551,378 | B2 | 10/2013 | Velev et al. |
| 8,975,387 | B1 | 3/2015 | Venditti et al. |
| 2006/0079494 | A1 | 4/2006 | Santi et al. |
| 2007/0178573 | A1 | 8/2007 | Cheetham et al. |
| 2010/0004234 | A1 | 1/2010 | Santi et al. |
| 2011/0171714 | A1 | 7/2011 | Cheetham et al. |
| 2012/0077775 | A1 | 3/2012 | Winssinger et al. |
| 2013/0053434 | A1 | 2/2013 | Winssinger et al. |
| 2013/0310265 | A1 | 11/2013 | Menegatti et al. |
| 2014/0155635 | A1 | 6/2014 | Sim et al. |

FOREIGN PATENT DOCUMENTS

| JP | 2015110624 A | 6/2015 |
| WO | 2006036941 A2 | 4/2006 |
| WO | 2008021213 A1 | 2/2008 |
| WO | 2012097049 A2 | 7/2012 |
| WO | 2013055780 A1 | 4/2013 |
| WO | 2014082085 A1 | 5/2014 |
| WO | 2015009701 A1 | 1/2015 |
| WO | 2015059177 A1 | 4/2017 |

OTHER PUBLICATIONS

Fakhouri. Bioorganic and Medicinal Chemistry, 2015, 23, 6993-6999 (Year: 2015).*
Wu, Xuefeng, et al, "Ubiquitin-conjugating enzyme Ubc13 controls breast cancer metastasis through a TAK1-p38 MAP kinase cascade," Proceedings of the National Academy of Sciences, vol. 111, Issue 38, 2014, National Academy of Sciences, pp. 1-6.
Xu, Jin et al., "Design, synthesis and biological evaluation of FLT3 covalent inhibitors with a resorcylic acid core," Bioorganic & Medicinal Chemistry, vol. 22, Issue 23, Oct. 12, 2014, Elsevier Ltd., pp. 6625-6637.
Xu, Jin, et al., "Exploring Aigialomycin D and Its Analogues as Protein Kinase Inhibitors for Cancer Targets," ACSMedicinal Chemistry Letters, vol. 2, Issue 9, 2011, American Chemical Society, pp. 662-666.
Xu, Jing, et al., "Recent progress regarding the bioactivities, biosynthesis and synthesis of naturally occuring resorcinolic macrolides," Acta Pharmacologica Sinica, vol. 35, Issue 3, Jan. 27, 2014, www.nature.com/aps, CPS and SIMM, pp. 316-330.
Xu, Liang-Xiong et al., "Absolute Configurations of Four Resorcylic Acid Lactones, Paecilomycins J M, by CD/TDDFT Calculations," vol. 26, Issue 1, Jan. 2014, Wiley Periodicals, Inc., pp. 44-50.
Xu, Liangxiong et al., "β-Resorcylic Acid Lactones from a Paecilomyces Fungus," Journal of Natural Products, vol. 73, Issue 5, Apr. 29, 2010, American Chemical Society and American Society of Pharmacognosy, pp. 885-889.
Xu, Yuquan et al., "Insights into the Biosynthesis of 12-Membered Resorcylic Acid Lactones from Heterologous Production in *Saccharomyces cerevisiae*," ACS Chemical Biology, vol. 9, Issue 5, Mar. 6, 2014, American Chemical Society, pp. 1119-1127.

(Continued)

*Primary Examiner* — Noble E Jarrell
(74) *Attorney, Agent, or Firm* — Julia A. Kim; In Vivo Patent Law

(57) ABSTRACT

This disclosure is directed to non-aromatic difluoro analogues of resorcylic acid lactones, pharmaceutical compositions comprising non-aromatic difluoro analogues of resorcylic acid lactones, and methods of treatment comprising non-aromatic difluoro analogues of resorcylic acid lactones.

5 Claims, 1 Drawing Sheet

(56) References Cited

OTHER PUBLICATIONS

Yamaguchi, Kyoko, et al., "Identification of a Member of the MAPKKK Family as a Potential Mediator of TGF-β Signal Transduction," Science, vol. 270, Dec. 22, 1995, American Association for the Advancement of Science, pp. 2008-2011.
Zawilska. Trends in Pharmacological Sciences, 2013, 65, 1-14 (Year: 2013).
Zea-Ponce, Yolanda et al., "Synthesis and in vitro evaluation of new benzovesamicol analogues as potential maging probes for the vesicular acetylcholine transporter," Bioorganic & Medicinal Chemistry, vol. 13, Issue 3, Nov. 11, 2004, Elsevier Ltd., pp. 745-753.
Zhang, Jianming, et al., "Targeting cancer with small molecule kinase inhibitors," Nature Reviews. Cancer, vol. 9, Issue 1, Jan. 2009, Macmillan Publishers Limited, pp. 28-39.
Zhou, Hui et al., "Enzymatic Synthesis of Resorcylic Acid Lactones by Cooperation of Fungal Iterative Polyketide Synthases Involved in Hypothemycin Biosynthesis," Journal of the American Chemical Society (JACS), vol. 132, Issue 13, Mar. 11, 2010, American Chemical Society, pp. 4530-4531.
"Metabolite", http:www.encyclopedia.com/doc/1E1-metabolithtml, accessed Jan. 25, 2008 (Year: 2008).
Acuña, Ulyana Muñoz et al., "Effects of (5Z)-7-Oxozeaenol on the Oxidative Pathway of Cancer Cells," Anticancer Research, vol. 32, Issue 7, Jul. 2012, The International Institute of Anticancer Research, pp. 2665-2671.
Ayers, Sloan et al., "Resorcylic Acid Lactones with Cytotoxic and NF-κB Inhibitory Activities and Their Structure-Activity Relationships," Journal of Natural Products, vol. 74, Issue 5, May 27, 2011, http://pubs.acs.org/doi/abs/10.1021/np200062x, American Chemical Society, pp. 1-12.
Barf, Tjeerd et al., "Irreversible Protein Kinase Inhibitors: Balancing the Benefits and Risks," Journal of Medicinal Chemistry, vol. 55, Issue 14, May 23, 2012, American Chemical Society, pp. 6243-6262.
Barluenga, Sofia et al., "In Vivo Efficacy of Natural Product-Inspired Irreversible Kinase Inhibitors," ChemBioChem, vol. 11, Issue 12, Aug. 16, 2010, Wiley-VCH Verlag GmbH& Co., pp. 1692-1699.
Barluenga, Sofia et al., "Resorcylic acid lactones: A pluripotent scaffold with therapeutic potential," Comptes Rendus Chimie, vol. 11, Issue 11, Nov.-Dec. 2008, Elsevier Masson SAS, pp. 1306-1317.
Bettermann, K. et al., "TAK1 Suppresses a NEMO-Dependent but NF-kB-Independent Pathway to Liver Cancer," Cancer Cell, vol. 17, Issue 5, May 18, 2010, Elsevier Inc., pp. 481-496.
Bolte, Benoit et al., "Modular Total Syntheses of the Marine-Derived Resorcylic Acid Lactones Cochliomycins A and B Using a Late-Stage Nozaki-Hiyama-Kishi Macrocyclization Reaction," The Journal of Organic Chemistry, vol. 80, Issue 1, Nov. 18, 2014, American Chemical Society, pp. 460-470.
Bosman, Matthieu Cornelis Johannes et al., "The TAK1-NF-kB axis as therapeutic target for AML, "Blood, vol. 124, Issue 20, The American Society of Hematology, pp. 3130-3140.
Cai, Patty C.H. et al, "Elevated TAK1 augments tumor growth and metastatic capacities of ovarian cancer cells through activation of NF-kB signaling,"Oncotarget, vol. 5, Issue 17, Jul. 27, 2014, Impact Journals, www.impactjournals.com/oncotarget, pp. 7549-7562.
Chrovian, Christa C. et al., "Total Synthesis of Aigialomycin D: Surprising Chemoselectivity Dependence on Alkyne Structure in Nickel-Catalyzed Cyclizations," Organic Letters, vol. 10, Issue 5, 2008, American Chemical Society, pp. 811-814.
Dean, Melissa A. et al., "Synthesis and application of oxadiazines as chiral ligands for the enantioselective addition of diethylzinc to aldehydes," Tetrahedron: Asymmetry, vol. 21, Oct. 26, 2010, Elsevier Ltd., pp. 2471-2478.
Dijkstra, Peter J., et al., "Use of Pyrylium Synthons in the Synthesis of Hemispherands with Modified Cavities. X-ray Structures of the 21-Hemispherand and a Pyrido Hemispherand," Journal of Organic Chemistry, vol. 52, Issue 12, 1987, American Chemical Society, pp. 2433-2442.
El-Elimat, Tamam et al., "Greensporones: Resorcylic Acid Lactones from an Aquatic *Halenospora* sp.," Journal of Natural Products, vol. 77, Issue 9, Aug. 5, 2014, American Chemical Society andAmerican Society of Pharmacognosy, pp. 2088-2098.
El-Elimat, Tamam M. et al., "Discovering New Structural Diversity from Unexplored Fungi," Thesis, The University of North Carolina at Greensboro, Doctor of Philosophy, Umi Number: 3624188, Greensboro, North Carolina, 2014, ProQuest LLC, 377 pages.
Ellestad, George A., et al., "New Zearalenone Related Macrolides and Isocoumarins from an Unidentified Fungus," Journal of Organic Chemistry, vol. 32, Issue 12, 1978, American Chemical Society, pp. 2339-2343.
Fakhouri, Lara, et al., "Isolation, semisynthesis, covalent docking and transforming growth factor beta-activated kinase 1 (TAK1) inhibitory activies of (5Z)-7-oxozeaenol analogues," Bioorganic & Medicinal Chemistry, vol. 23, Issue 21, Nov. 1, 2015, Elsevier Ltd., pp. 1-9.
Fandong, Meng, et al., "Identification of TGF-β-activated kinase 1 as a possible novel target for renal cell carcinoma intervention," Biochemical and Biophysical Research Communications, vol. 453, 2014, Elsevier Inc., pp. 106-111.
Giroux, Valentin et al., "Probing the human kinome for kinases involved in pancreatic cancer cell survival and gemcitabine resistance," The FASEB Journal, vol. 20, Issue 12, 2006, Federation of American Societies for Experimental Biology, pp. 1982-1991.
Gong, Yi-Nan et al., "Chemical probing reveals insights into the signaling mechanism of inflammasome activation," Cell Research, vol. 20, Issue 12, Dec. 2010, Nature Publishing Group, pp. 1289-1305.
Goto, Masaki et al., "E6201 [(3S,4R,5Z,8S,9S,11E)-14-(Ethylamino)-8, 9,16-trihydroxy-3,4-dimethyl-3,4,9,19-tetrahydro-1H-2-benzoxacyclotetradecine-1,7 (8H)-dione], a Novel Kinase Inhibitor of Mitogen-Activated Protein Kinase/Extracellular Signal-Regulated Kinase Kinase (MEK)-1 and MEK Kinase-1: In Vitro Characterization of Its Anti-Inflammatory and Antihyperproliferative Activities." The Journal of Pharmacology and Experimental Therapeutics, vol. 331, Issue 2, 2009, pp. 485-495.
Griffioen, Arjan W. et al., "Angiogenesis: Potentials for Pharmacologic Intervention in the Treatment of Cancer, Cardiovascular Diseases, and Chronic Inflammation," Pharmacological Reviews, vol. 52, Issue 2, 2000, American Society for Pharmacology and Experimental Therapeutics, pp. 237-268.
Han, Myung Woul et al., "Autophagy Inhibition Can Overcome Radioresistance in Breast Cancer Cells Through Suppression of TAK1 Activation," Anticancer Research, vol. 34, Issue 3, 2014, The International Institute of Anticancer Research, pp. 1449-1455.
Harvey, Alan L., "The re-emergence of natural products for drug discovery in the genomics era," Nature Reviews Drug Discovery, vol. 14, Jan. 23, 2015, Macmillan Publishers Limited, pp. 1-19.
Heberlig, Graham W. et al., "Resorcylic Acid Lactone Biosynthesis Relies on a Stereotolerant Macrocyclizing Thioesterase," Organic Letters, vol. 16, Issue 22, Nov. 5, 2014, American Chemical Society, pp. 5858-5861.
Hellwig, Veronika et al., "Pochonins A-F, New Antiviral and Antiparasitic Resorcylic Acid Lactones from *Pochonia chlamydosporia* var. catenulata," Journal of Natural Products, vol. 66, Issue 6, Jun. 3, 2003, American Chemical Society and American Society of Pharmacognosy, pp. 829-837.
Hildebrand, Andreas, et al., "Aromatic hydroxylation and catechol formation: A novel metabolic pathway of the growth promotor zeranol," Toxicology Letters, vol. 192, Issue 3, 2010, Elsevier Ireland Ltd., pp. 379-386.
Hofmann, Tatjana et al., "Resorcylic acid lactones as new lead structures for kinase inhibition," Comptes Rendus Chimie, vol. 11, Issue 11, Nov.-Dec. 2008, Elsevier Masson SAS, pp. 1318-1335.
Hofmann, Tatjana, "Resorcylic lactone L-783277 as a new lead structure for kinase inhibition total synthesis and SAR studies," Doctoral Thesis, Diss. ETH No. 18336, Swiss Federal Institute of Technology Zurich, Germany, 2009, ETH Library, 8 pages.

(56) References Cited

OTHER PUBLICATIONS

Ikemori-Kawada, Megumi et al., "Conformational Analyses and MO Studies of f152A1 and Its Analogues as Potent Protein Kinase Inhibitors," Journal of Chemical Information and Modeling, vol. 49, Issue 12, Dec. 2009, American Chemical Society, pp. 2650-2659.

Ikeuchi, Tomoko et al., "A vitamin D3 analog augmented interleukin-8 production by human monocytic cells in response to various microbe-related synthetic ligands, especially NOD2 agonistic muramyldipeptide," International Immunopharmacology, vol. 15, Issue 1, Jan. 2013, Elsevier B.V., pp. 15-22.

International Preliminary Report on Patentability for International Patent Application No. PCT/US2016/034562, dated Dec. 14, 2017, 8 pages.

International Search Report and Written Opinion for International Patent Application No. PCT/US2016/034562, dated Apr. 11, 2017, 11 pages.

Jackson-Bernitsas, DG et al., "Evidence that TNF-TNFR1-TRADD-TRAF2-RIP-TAK1-IKK pathway mediates constitutive NF-kB activation and proliferation in human head and neck squamous cell carcinoma," Oncogene, vol. 26, Issue 10, Sep. 4, 2006, Nature Publishing Group, pp. 1385-1397.

Janin, Yves L., "Heat Shock Protein 90 Inhibitors. A Text Book Example of Medicinal Chemistry?," Journal of Medicinal Chemistry, vol. 48, Issue 24, Dec. 1, 2005, American Chemical Society, pp. 7503-7512.

Jogireddy, Rajamalleswaramma et al., "Molecular Editing of Kinase-Targeting Resorcylic Acid Lactones (RAL): Fluoroenone RAL," ChemMedChem, vol. 5, Issue 5, May 3, 2010, Wiley-VCH Verlag GmbH& Co., pp. 670-673.

Jogireddy, Rajamalleswaramma et al., "Synthesis of a Resorcylic Acid Lactone (RAL) Library Using Fluorous-Mixture Synthesis and Profile of its Selectivity Against a Panel of Kinases," Chemistry—A European Journal, vol. 15, Issue 43, 2009, Wiley-VCH Verlag 11498 GmbH&Co., pp. 11498-11506.

Johnson, G. L, et al., "MAPK kinase kinases (MKKKs) as a target class for small-molecule inhibition to modulate signaling networks and gene expression," Current Opinion in Chemical Biology, vol. 9, Issue 3, Jun. 2005, Elsevier Ltd., pp. 325-331.

Kamiyama, Hiroshi et al., "Epoxyquinol B, a Naturally Occurring Pentaketide Dimer, Inhibits NF-κB Signaling by Crosslinking TAK1," Bioscience, Biotechnology, and Biochemistry, vol. 72, Issue 7, 2008, Japan Society for Bioscience, Biotechnology and Agrochemistry, pp. 1894-1900.

Kashima, Takasumi et al., "Biosynthesis of Resorcylic Acid Lactone Lasiodiplodin in Lasiodiplodia theobromae," Bioscience, Biotechnology, and Biochemistry, vol. 73, Issue 5, May 2009, Japan Society for Bioscience, Biotechnology, and Agrochemistry (JSBBA), pp. 1118-1122.

Kataoka, Takao, "Chemical biology of inflammatory cytokine signaling," The Journal of Antibiotics, vol. 62, Issue 12, Dec. 2009, Japan Antibiotics Research Association, pp. 655-667.

Khadem, Shahriar et al., "Monocyclic Phenolic Acids; Hydroxy- and Polyhydroxybenzoic Acids: Occurrence and Recent Bioactivity Studies," Molecules, vol. 15, Nov. 8, 2010, www.mdpi.com/journal/molecules, pp. 7985-8005.

Khartulyari, Anton S., "Concise Strategy to the Core Structure of the Macrolide Queenslandon," Organic Letters, vol. 8, Issue 25, Nov. 8, 2006, American Chemical Society, pp. 5833-5836.

Khartulyari, Anton S., "Synthesis of Benzomorphan Scaffolds by Intramolecular Buchwald-Hartwig Arylation and Approach Towards the Total Synthesis of the Macrolide Queenslandon," Thesis, Faculty of Chemistry and Pharmacy the Eberhard-Karls-University Tübingen, 2007, 279 pages.

Kilty, Iain, et al., "TAK1 Inhibition in the DFG-Out Conformation," Chemical Biology & Drug Design, vol. 82, Issue 5, John Wiley & Sons A/S, pp. 500-505.

Kondo, Masashi, et al., "Molecular cloning of human TAK1 and its mutational analysis in human lung cancer," International Journal of Cancer, vol. 75, Issue 4, 1998, Wiley-Liss, Inc., pp. 559-563.

Kuk, Hanna, "TAK1 Mediates TGF beta-1 Responses in Gingival Fibroblasts," The University of Western Ontario, Electronic Thesis and Dissertation Repository, London, Ontario, Canada, 2014, https://ir.lib.uwo.ca/etd/1980, 125 pages.

Kumarasamy, Y., "Scaling-up of natural products isolation," Methods in Molecular Biology, vol. 864, 2012, Springer, pp. 465-472 Abstract.

Langlois, Bernard R., et al., "Trifluoromethylation of Aromatic Compounds with Sodium Trifluoromethanesulfinate under oxidative conditions," Tetrahedron Letters, vol. 32, Issue 51, 1991, Pergamon Press PLC, pp. 7525-7528.

Leproult, Emeline et al., "Cysteine Mapping in Conformationally Distinct Kinase Nucleotide Binding Sites: Application to the Design of Selective Covalent Inhibitors," Journal of Medicinal Chemistry, vol. 54, Issue 5, Feb. 15, 2011, American Chemical Society, pp. 1347-1355.

Liniger, Marc, et al., "Kinase Inhibition by Deoxy Analogues of the Resorcylic Lactone L-783277," ACS Medicinal Chemistry Letters, vol. 20, Issue 2, Oct. 20, 2010, American Chemical Society, pp. 22-27.

Liu, Jing et al, "Natural products as kinase inhibitors," Natural Product Reports, vol. 29, Issue 3, Mar. 2012, Royal Society of Chemistry, pp. 392-403.

Liu, Qingsong et al., "Developing Irreversible Inhibitors of the Protein Kinase Cysteinome," Chemistry & Biology, vol. 20, Issue 2, Feb. 21, 2013, Elsevier Ltd., pp. 146-159.

Makita, Masanori, et al., "Antilung Cancer Effect of WT1-specific Cytotoxic T Lymphocytes," Clinical Cancer Research, vol. 8, Aug. 2002, American Association for Cancer Research, pp. 2626-2631.

Mallinson, Jamie el al., "Macrocycles in new drug discovery," Future Medicinal Chemistry, vol. 4, Issue 11, 2012, Future Science Ltd., pp. 1409-1438.

Matos, Marie-Christine et al., "Synthesis of Macrolide-Saccharide Hybrids by Ring-Closing Metathesis of Precursors Derived from Glycitols and Benzoic Acids," The Journal of Organic Chemistry, vol. 72, Issue 5, Mar. 2, 2007, American Chemical Society, pp. 1803-1806.

Melisi, Davide, et al., Modulation of Pancreatic Cancer Chemoresistance by Inhibition of TAK1, vol. 103, Issue 15, Aug. 3, 2011, Oxford University Press, pp. 1190-1204.

Min, Kyung-Won et al., "Nordihydroguaiaretic acid suppresses the lipopolysaccharide-induced activation of macrophage through the down-regulation of TAK1," Animal Cells and Systems, vol. 17, Issue 1, 2013, Korean Society for Integrative Biology, pp. 15-22.

Miyatake-Ondozabal, Hideki, "A Novel Biomimetic Synthesis of Resorcytic Acid Lactones; Via Macrolactonization and Transannular Aromatization," Doctor of Philosophy Thesis, Imperial College, South Kensington, London, May 2012, 260 pages.

Miyatake-Ondozabal, Hideki, "Total Synthesis of TAK-Kinase Inhibitor LL-Z1640-2 via Consecutive Macrocyclization and Transannular Aromatization," Organic Letters, vol. 12, Issue 23, Nov. 10, 2010, American Chemical Society, pp. 5573-5575.

Mohan, Chandra et al., "NF-κB Activation: A Molecular Link Between Chronic Inflammation and Cancer," Research Focus, vol. 1, 2013, EMD Millipore Corporation, pp. 1-12.

Moulin, Emilie, "Diversity-Oriented Synthesis of Pochonins a Privilege Scaffold for ATP ASE and Kinase Inhibition," Thesis PhD, Doctor of Louis Pasteur University from Strasbourg, Institute of Supramolecular Science and Engineering Laboratory of Organic and Bioorganic Chemistry, 2006, 269 pages.

Muramoto, Kenzo, "The regulation of immune response by a novel kinase inhibitior E6201 and EP4 antagonists," Kumamoto University Repository System, Thesis or Dissertation, Jan. 14, 2011, http://hdl.handle.net/22913/22144, 136 pages.

Napolitano, Carmela et al., "Isosteric replacement of the Z-enone with haloethyl ketone and E-enone in a resorcylic acid lactone series and biological evaluation," Bioorganic & Medicinal Chemistry Letters, vol. 21, Issue 4, Feb. 15, 2011, Elsevier Ltd., pp. 1167-1170.

Napolitano, Carmela et al., "Synthesis, kinase activity and molecular modeling of a resorcylic acid lactone incorporating an amide and a trans-enone in the macrocyde," Tetrahedron, vol. 68, Issue 27, Apr. 28, 2012, Elsevier Ltd., pp. 5533-5540.

(56) References Cited

OTHER PUBLICATIONS

Napolitano, Carmela, et al., "Access to Resorcylic Acid Lactones via Phosphonate Based Intramolecular Olefination," Journal of Organic Chemistry, vol. 75, Issue 21, Oct. 12, 2010, American Chemical Society, pp. 7404-7407.

Navarro, Ismael et al., "Biomimetic Synthesis of Resorcylate Natural Products Utilizing Late Stage Aromatization: Concise Total Syntheses of the Marine Antifungal Agents 15G256l and 15G256β," Journal of the American Chemical Society, vol. 130, Issue 31, Jul. 9, 2008, American Chemical Society, pp. 10293-10298.

Neil, Jason Robert, "TGF-β Promotes Cancer Progression Through the xIAP: TAB1:IKK Axis in Mammary Epithelial Cells," Thesis, Doctor of Philosophy, UMI No. 3325836, University of Colorado, Aug. 5, 2008, ProQuest LLC, 160 pages.

Nguyen, Duy (Leo), "Rescue of ΔF508-CFTR by Kinase Inhibitors," Thesis, Master of Science, Graduate Department of Biochemistry, University of Toronto, 2013, 134 pages.

Ninomiya-Tsuji, Jun, et al., "A Resorcylic Acid Lactone, 5Z-7-Oxozeaenol, Prevents Inflammation by Inhibiting the Catalytic Activity of TAK1 MAPK Kinase Kinase," The Journal of Biological Chemistry, vol. 278, Issue 20, Mar. 6, 2003, JBC Papers in Press, pp. 18485-18490.

Ninomiya-Tsuji, Jun, et al., "The kinase TAK1 can activate the NIK-IkB as well as the MAP kinase cascade in the IL-1 signalling pathway," Nature, vol. 398, Mar. 18, 1999, Macmillan Magazines Ltd, pp. 252-256.

Nishino, Mari et al., "Hypothemycin, a fungal natural product, identifies therapeutic targets in Trypanosoma brucei," ?eLIFE, vol. 2, Jul. 9, 2013, pp. 1-15.

Pace, Nicholas J. et al., "Diverse Functional Roles of Reactive Cysteines," ACS Chemical Biology, vol. 8, Issue 2, Nov. 19, 2012, American Chemical Society, pp. 283-296.

Patel, Bhavesh H. et al., "Conversion of α-Amino Acids into Bioactive o-Aminoalkyl Resorcylates and Related Dihydroxyisoindolinones," The Journal of Organic Chemistry, vol. 76, Issue 15, Jun. 6, 2011, American Chemical Society, pp. 6209-6217.

Pauls, Eduardo et al., "Essential Role for IKKβ in Production of Type 1 Interferons by Plasmacytoid Dendritic Cells," The Journal of Biological Chemistry, vol. 287, Issue 23, Jun. 1, 2012, The American Society for Biochemistry and Molecular Biology, Inc., pp. 19216-19228.

Postler, Thomas S. et al., "The Cytoplasmic Domain of the HIV-1 Glycoprotein gp41 Induces NF-κB Activation through TGF-β-Activated Kinase 1," Cell Host & Microbe, vol. 11, Issue 2, Feb. 16, 2012, Elsevier Inc., pp. 181-193.

Rawlins, Philip et al., "Inhibition of endotoxin-induced TNF-α production in macrophages by 5Z-7-oxo-zeaenol and other fungal resorcylic acid lactones," International Journal of Immunopharmacology, vol. 21, Issue 12, Dec. 1999, Elsevier Science Ltd., pp. 799-814.

Robertson, Murray N., "Studies towards a fast and efficient total synthesis of LL-Z1640-2," PhD Thesis, University of Glasglow, Department of Chemistry, Feb. 2009, http://theses.gla.ac.uk/610/, 148 pages.

Sakurai, Hiroaki, "Targeting of TAK1 in inflammatory disorders and cancer," Trends in Pharmacological Sciences, vol. 33, Issue 10, Oct. 2012, Elsevier Inc., pp. 522-530.

Sakurai, Trends in Pharmacological Sciences, 2012, 33 (10), 522-30 (Year 2012).

Schmidt, Bernd, et al., "A Cross-Metathesis-Conjugate Addition Route to Enantiopurey-Butyrolactams and γ-Lactones from a C2-Symmetric Precursor," European Journal of Organic Chemistry, vol. 2011, Issue 9, 2011, Wiley-VCH Verlag GmbH & Co. KGaA, Weinheim, pp. 1721-1727.

Schuman, James, et al., "A critical role of TAK1 in B-cell receptor-mediated nuclear factor κB activation," Blood, vol. 113, Issue 19, May 7, 2009, The American Society of Hematology, 14 pages.

Shao, Chang-Lun et al., "Potent Antifouling Resorcylic Acid Lactones from the Gorgonian-Derived Fungus Cochliobolus lunatus," Journal of Natural Products, vol. 74, Issue 4, Feb. 24, 2011, The American Chemical Society and American Society of Pharmacognosy, pp. 629-633.

Shao, Chung-Lun, et al., "Structure and Absolute Configuration of Fumiquinazoline L, an Alkaloid from a Gorgonian-Derived *Scopulariopsis* sp. Fungus," Journal of Natural Products, vol. 76, Issue 4, Apr. 15, 2013, The American Chemical Society and American Society of Pharmacognosy, 4 pages.

Singh, Anurag, et al., "TAK1 Inhibition Promotes Apoptosis in KRAS-Dependent Colon Cancers," Cell, vol. 148, Issue 4, Feb. 17, 2012, Elsevier Inc., pp. 639-650.

Singh, Juswinder et al., "The resurgence of covalent drugs," Nature Reviews, vol. 10, Issue 4, Apr. 2011, Macmillan Publishers Limited, pp. 307-317.

Smith, David F. et al., "Molecular Chaperones: Biology and Prospects for Pharmacological Intervention," Pharmacological Reviews, vol. 50, Issue 4, Dec. 1998, The American Society for Pharmacology and Experimental Therapeutics, pp. 493-513.

Smith, Eric W. et al., "Chapter 15.4: Electroporation," Percutaneous Penetration Enhancers (book), 1995, Boca Raton, Florida, CRC Press, Inc., 15 pages.

Smyth, Lynette et al., "Design and evaluation of 3-aminopyrazolopyridinone kinase inhibitors inspired by the natural product indirubin," Bioorganic & Medicinal Chemistry, vol. 19, Issue 11, Apr. 13, 2011, Elsevier Ltd., pp. 3569-3578.

Tak, Paul P. et al., "NF-κB: a key role in inflammatory diseases," The Journal of Clinical Investigation, vol. 107, Issue 1, Jan. 2001, American Society for Clinical Investigation (ASCI), pp. 7-11.

Tan, Li et al, "Discovery of Type II Inhibitors of TGFβ-Activated Kinase 1 (TAK1) and Mitogen-Activated Protein Kinase Kinase Kinase 2 (MAP4K2)," Journal of Medicinal Chemistry, vol. 58, Issue 1, Jul. 17, 2014, American Chemical Society, pp. 183-196.

Valot, Gaëlle, "Extending the diversity of privileged natural product motifs: Synthesis of a library of resorcylic acid lactones and studies towards the guaianes and pseudoguaianes," University of Strasbourg, PhD Thesis, May 13, 2011, cnrs, 265 pages.

Wang, Jiang, et al., "Fluorine in Pharmaceutical Industry: Fluorine-Containing Drugs Introduced to the Market in the Last Decade (2001-2011)," Chemical Reviews, vol. 114, Issue 4, Dec. 3, 2013, American Chemical Society, 75 pages.

Wang, Shuhao et al., "Functional Characterization of the Biosynthesis of Radicicol, an Hsp90 Inhibitor Resorcylic Acid Lactone from Chaetomium chiversii," Chemistry & Biology, vol. 15, Issue 12, Dec. 22, 2008, Elsevier Ltd., pp. 1328-1338.

Wang, Yiting, et al., "CXC195 suppresses proliferation and inflammatory response in LPS-induced human hepatocellular carcinoma cells via regulating TLR4-MyD88-TAK1-mediated NF-kB and MAPK pathway," Biochemical and Biophysical Research Communications, 2014, Elsevier Inc., pp. 1-7.

Winssinger, Nicolas et al., "Chemistry and biology of resorcylic acid lactones," Chem Commun (Camb), vol. 1, Sep. 25, 2006, Royal Society of Chemistry, pp. 22-36.

Wirz, Monica Hélène, "Characterizing the Macrocyclization Activity of Fungal Polyketide Synthase Thioesterases," Thesis, Department of Chemistry, University of Ottawa, Ontario, Canada, Dec. 2011, 252 pages.

Woodhead, Andrew J., et al., "Discovery of (2,4-Dihydroxy-5-isopropylphenyl)-[5-(4-methylpiperazin-1-ylmethyl)-1,3-dihydroisoindol-2-yl]methanone (AT13387), a Novel Inhibitor of the Molecular Chaperone Hsp90 by Fragment Based Drug Design," Journal of Medicinal Chemistry, vol. 53, Issue 16, Jul. 28, 2010, American Chemical Society, pp. 5956-5969.

Wu, Huifang, et al., "Position of Coordination of the Lithium Ion Determines the Regioselectivity of Demethylations of 3,4-Dimethoxymorphinans with L-Selectride," Organic Letters, vol. 7, Issue 13, May 27, 2005, American Chemical Society, 4 pages.

Wu, Jiaquan, et al., "Mechanism and in Vitro Pharmacology of TAK1 Inhibition by (5Z)-7-Oxozeaenol," ACS Chemical Biology, vol. 8, Dec. 28, 2012, American Chemical Society, pp. 643-650.

\* cited by examiner

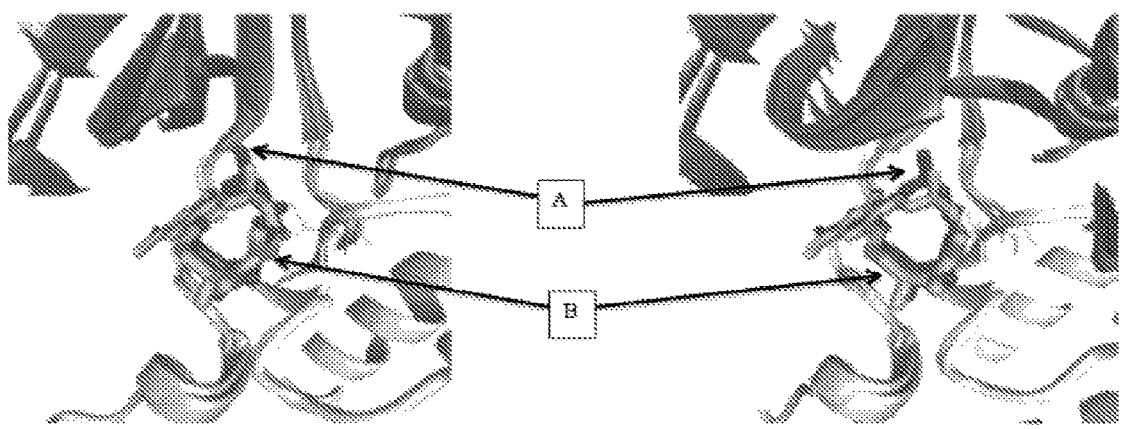

NON-AROMATIC DIFLUORO ANALOGUES OF RESORCYLIC ACID LACTONES

CROSS REFERENCE TO RELATED APPLICATIONS

This application is a divisional of U.S. application Ser. No. 15/579,251 filed Dec. 4, 2017, which is a 35 U.S.C. § 371 national phase application of PCT Application PCT/US16/034562 filed May 27, 2016, which claims priority to U.S. Provisional Patent Application No. 62/170,789 filed on Jun. 4, 2015. The contents of each are hereby incorporated by reference in their entirety.

STATEMENT REGARDING FEDERALLY SPONSORED RESEARCH OR DEVELOPMENT

This invention was made with government support under Grant CA125066 awarded by the National Cancer Institute at the National Institutes of Health. The United States Government has certain rights in the invention.

1. FIELD

The invention relates generally to the discovery of novel resorcylic acid lactones analogues.

2. BACKGROUND (5Z)-7-Oxozeaenol is a β-resorcylic acid lactone that was first isolated in 1978 by Ellestad et al from an unidentified fungus.[1] At that time, this secondary metabolite was of no potential clinical value since it lacked any anabolic activity, unlike other previously isolated and structurally related zearalenones. In 2003, during screening for inhibitory activity against transforming growth factor-β-activated kinase 1 (TAK-1), (5Z)-7-oxozeaenol was found to be a potent inhibitor of the aforementioned enzyme with an $IC_{50}$ of 8.1 nM.[2] Similar to almost all kinase inhibitors,[11] (5Z)-7-oxozeaenol is a competitive ATP ligand and binds irreversibly to its target.[2] This irreversible interaction was validated when the covalently-bound ligand was cocrystallized with TAK-1.[12]

Although (5Z)-7-oxozeaenol (1) is a potent inhibitor of the potentially important target TAK-1, for treatment of inflammation and cancer, its progress to move to the clinic is halted mainly because of its instability in plasma.[16] There is an explicit need to diversify this important scaffold to potentially provide more active analogues.

Thus, there is a need to develop novel resorcylic acid lactones analogues.

3. SUMMARY OF THE DISCLOSURE

The presently disclosed subject matter provides non-aromatic difluoro analogues of resorcylic acid lactones, pharmaceutical compositions comprising non-aromatic difluoro analogues of resorcylic acid lactones, and methods of treatment comprising non-aromatic difluoro analogues of resorcylic acid lactones.

In some embodiments, the presently disclosed subject matter is directed to compounds of the general formula (I):

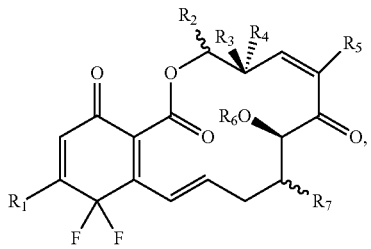

or a pharmaceutically acceptable derivative thereof; wherein $R_1$ is halogen, hydrogen, hydroxyl, hydroxyl with an oxygen protecting group, $NR_7R_8$, $OR_7$, $SR_7$, $—X_1(CH_2)_pX_2—R_9$, or is lower alkyl optionally substituted with amino, halogen, hydroxyl, hydroxyl with an oxygen protecting group, protected amino, or $—X_1(CH_2)_pX_2—R_9$;
wherein $R_7$ and $R_8$ are, independently for each occurrence, $C_2$-$C_{20}$ alkenyl, $C_1$-$C_{20}$ alkyl, $C_2$-$C_{20}$ alkynyl, $C_3$-$C_{14}$ aryl, $C_3$-$C_{20}$ cycloalkenyl, $C_3$-$C_{20}$ cycloalkyl, $C_3$-$C_{20}$ cycloalkynyl, $C_2$-$C_{20}$ heteroalkenyl, $C_1$-$C_{20}$ heteroalkyl, $C_2$-$C_{20}$ heteroalkynyl, $C_3$-$C_{14}$ heteroaryl, $C_3$-$C_{20}$ heterocycloalkenyl, $C_3$-$C_{20}$ heterocycloalkyl, $C_3$-$C_{20}$ heterocycloalkynyl, or hydrogen; or a nitrogen or oxygen protecting group, or $R_7$ and $R_8$, taken together may form a saturated or unsaturated cyclic ring of 1 to 4 carbon atoms and 1 to 3 nitrogen or oxygen atoms, and each of $R_7$ and $R_8$ are optionally further substituted with one or more alkylamino, alkyloxy, amino, aminoalkyl, halogen, hydroxyl, hydroxyl with an oxygen protecting group, or protected amino,
wherein $X_1$ and $X_2$ are each independently absent, or are $—N(alkyl)$, NH, or oxygen, or wherein $X_2—R_9$ together are $N_3$ or are a saturated or unsaturated heterocyclic moiety;
p is 2-10, and
$R_9$ is hydrogen, or a $C_1$-$C_{20}$ alkyl($C_3$-$C_{14}$)aryl, $C_1$-$C_{20}$ alkyl($C_3$-$C_{14}$)heteroaryl, $C_3$-$C_{14}$ aryl, $C_3$-$C_{14}$ heteroaryl moiety, or is $—(C=O)NHR_{10}$, $—(C=O)OR_{10}$, or $—(C=O)R_{10}$, wherein each occurrence of $R_{10}$ is independently $C_2$-$C_{20}$ alkenyl, $C_1$-$C_{20}$ alkyl, $C_7$-$C_{20}$ alkynyl, $C_3$-$C_{14}$ aryl, $C_3$-$C_{20}$ cycloalkenyl, $C_3$-$C_{20}$ cycloalkyl, $C_3$-$C_{20}$ cycloalkynyl, $C_2$-$C_{20}$ heteroalkenyl, $C_1$-$C_{20}$ heteroalkyl, $C_2$-$C_{20}$ heteroalkynyl, $C_3$-$C_{14}$ heteroaryl, $C_3$-$C_{20}$ heterocycloalkenyl, $C_3$-$C_{20}$ heterocycloalkyl, $C_3$-$C_{20}$ heterocycloalkynyl, or hydrogen; or $R_9$ is $—SO_2(R_{11})$, wherein $R_{11}$ is a $C_2$-$C_{20}$ alkenyl, $C_1$-$C_{20}$ alkyl, or $C_2$-$C_{20}$ alkynyl moiety, wherein one or more of $R_9$, $R_{10}$, or $R_{11}$ are optionally substituted with one or more alkylamino, alkyloxy, amino, aminoalkyl, halogen, hydroxyl, hydroxyl with an oxygen protecting group, or protected amino;
$R_2$ is $C_2$-$C_{20}$ alkenyl, $C_1$-$C_{20}$ alkyl, $C_2$-$C_{20}$ alkynyl, $C_3$-$C_{14}$ aryl, $C_3$-$C_{20}$ cycloalkenyl, $C_3$-$C_{20}$ cycloalkyl, $C_3$-$C_{20}$ cycloalkynyl, $C_2$-$C_{20}$ heteroalkenyl, $C_1$-$C_{20}$ heteroalkyl, $C_2$-$C_{20}$ heteroalkynyl, $C_3$-$C_{14}$ heteroaryl, $C_3$-$C_{20}$ heterocycloalkenyl, $C_3$-$C_{20}$ heterocycloalkyl, $C_3$-$C_{20}$ heterocycloalkynyl, or hydrogen;
$R_3$ and $R_5$ are each independently halogen or hydrogen;
$R_4$ is halogen, hydrogen, or methyl;
$R_6$ is hydrogen or an oxygen protecting group;
$R_7$ is hydrogen, hydroxyl, or hydroxyl with an oxygen protecting group;
wherein oxygen protecting groups are selected from the group consisting of acetate, benzoate, benzyl ethers, benzyloxymethyl ether, carbonates, cyclic acetals, dichloroacetate, esters, ethyl ethers, formate, ketals, methoxymethyl ether, methylthiomethyl ether, methyl ethers, p-methoxybenzyloxymethyl ether, silyl ethers, t-butyldimethylsilyl ether, t-butyldiphenyl silyl ether, tribenzyl silyl ether, triethylsilylether, trifluoroacetate, triisopropylsilyl ether, and trimethylsilyl ether and wherein nitrogen protecting groups are selected from the group consisting of amides, carbamates, cyclic imides, enamines, imines, N-alkyl amines, N-aryl amines, and Troc; and wherein $C_3$-$C_{14}$ heteroaryl moieties are selected from cyclic aromatic moieties having from five to ten ring atoms of which one ring atom is selected from N, O, and S; zero, one or two ring atoms are additional heteroatoms independently selected from N, O, and S; and the remaining ring atoms are carbon.

In some embodiments, the presently disclosed subject matter is directed to compounds of the general formula (II):

or a pharmaceutically acceptable derivative thereof; wherein

V------W is $CH_2CH_2$, CH=CH, or

Y------Z is $CH_2CH_2$,

—$CH_2C(=O)$—,

CH=CH, or;

$R_{12}$ is hydrogen, hydroxyl, or methyl;

$R_{13}$, $R_{15}$, and $R_{17}$ may each independently be present or absent and if present $R_{13}$, $R_{15}$, and $R_{17}$ are each independently hydrogen or hydroxyl;

$R_{14}$ and $R_{16}$ are each independently hydrogen or hydroxyl;

wherein $R_{12}$ and $R_{13}$, when taken together, may optionally be =O wherein $R_{13}$ and $R_{14}$, when taken together, may optionally be;

wherein $R_{14}$ and $R_{16}$, when taken together, may optionally be and
$R_{18}$ is $C_1$-$C_{20}$ alkyl, hydrogen, methyl, or In some embodiments, the presently disclosed subject matter provides pharmaceutical compositions comprising the compounds of formula (I). In other embodiments, the compound is present in an amount effective to inhibit MAP3K. In other embodiments, the compound is present in an amount effective to inhibit TAK-1. In some embodiments, the presently disclosed subject matter provides pharmaceutical compositions comprising the compounds of formula (II). In other embodiments, the compound is present in an amount effective to inhibit MAP3K. In other embodiments, the compound is present in an amount effective to inhibit TAK-1.

In some embodiments, the presently disclosed subject matter provides a method for use of the compounds of formula (I) in the treatment of various disorders as described herein, comprising administering to a subject in need thereof a therapeutically effective amount of a compound of formula (I), and a pharmaceutically acceptable carrier or diluent. In certain embodiments, the present disclosed subject matter provides a method for treating cancer comprising administering to a subject in need thereof a therapeutically effective amount of a compound of Formula (I), and a pharmaceutically acceptable carrier or diluent. In some embodiments, the cancer is hepatocellular carcinoma, renal cell carcinoma, breast cancer, head and neck squamous cell carcinoma, pancreatic cancer, lung cancer, colon cancer, leukemia, or ovarian cancer. In some embodiments, the presently disclosed subject matter provides a method for use of the compounds of formula (II) in the treatment of various disorders as described herein, comprising administering to a subject in need thereof a therapeutically effective amount of a compound of formula (II), and a pharmaceutically acceptable carrier or diluent. In certain embodiments, the present disclosed subject matter provides a method for treating cancer comprising administering to a subject in need thereof a therapeutically effective amount of a compound of Formula (II), and a pharmaceutically acceptable carrier or diluent. In some embodiments, the cancer is hepatocellular carcinoma, renal cell carcinoma, breast cancer, head and neck squamous cell carcinoma, pancreatic cancer, lung cancer, colon cancer, leukemia, or ovarian cancer.

4. BRIEF DESCRIPTION OF THE FIGURE

FIG. 1 shows two perspective images of the same covalent docking output (darker shaded portions, for example at A) superimposed with the cocrystallized (5Z)-7-oxozeaenol (lighter shaded portions, for example at B). Parts of the enzyme's residues, in the binding pocket, are not shown in order to provide full perspective views of the covalent docking output superimposed with the cocrystallized (5Z)-7-oxozeaenol.

5. DETAILED DESCRIPTION OF THE DISCLOSURE

The presently disclosed subject matter provides non-aromatic difluoro analogues of resorcylic acid lactones, pharmaceutical compositions comprising non-aromatic difluoro analogues of resorcylic acid lactones, and methods of treatment comprising non-aromatic difluoro analogues of resorcylic acid lactones.

The presently disclosed subject matter now will be described more fully hereinafter. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

Unless defined otherwise, all technical and scientific terms used herein have the same meanings as commonly understood by one of ordinary skill in the art to which this disclosure belongs. Preferred methods, devices, and materials are described, although any methods and materials similar or equivalent to those described herein can be used in the practice or testing of the present disclosure. All references cited herein are incorporated by reference in their entirety. Numerical ranges are provided for certain quantities. It is to be understood that these ranges comprise all subranges therein. Thus, the range "from 50 to 80" includes all possible ranges therein (e.g., 51-79, 52-78, 53-77, 54-76, 55-75, 60-70, etc.). Furthermore, all values within a given range may be an endpoint for the range encompassed thereby (e.g., the range 50-80 includes the ranges with endpoints such as 55-80, 50-75, etc.).

I. Compounds

In some embodiments, the presently disclosed subject matter is directed to compounds of the general formula (I):

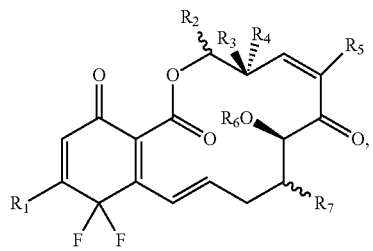

or a pharmaceutically acceptable derivative thereof; wherein
$R_1$ is halogen, hydrogen, hydroxyl, hydroxyl with an oxygen protecting group, $NR_7R_8$, $OR_7$, $SR_7$, —$X_1(CH_2)_pX_2$—$R_9$, or is lower alkyl optionally substituted with amino, halogen, hydroxyl, hydroxyl with an oxygen protecting group, protected amino, or —$X_1(CH_2)_pX_2$—$R_9$;

wherein $R_7$ and $R_8$ are, independently for each occurrence, $C_2$-$C_{20}$ alkenyl, $C_1$-$C_{20}$ alkyl, $C_2$-$C_{20}$ alkynyl, $C_3$-$C_{14}$ aryl, $C_3$-$C_{20}$ cycloalkenyl, $C_3$-$C_{20}$ cycloalkyl, $C_3$-$C_{20}$ cycloalkynyl, $C_2$-$C_{20}$ heteroalkenyl, $C_1$-$C_{20}$ heteroalkyl, $C_2$-$C_{20}$ heteroalkynyl, $C_3$-$C_{14}$ heteroaryl, $C_3$-$C_{20}$ heterocycloalkenyl, $C_3$-$C_{20}$ heterocycloalkyl, $C_3$-$C_{20}$ heterocycloalkynyl, or hydrogen; or a nitrogen or oxygen protecting group, or $R_7$ and $R_8$, taken together may form a saturated or unsaturated cyclic ring of 1 to 4 carbon atoms and 1 to 3 nitrogen or oxygen atoms, and each of $R_7$ and $R_8$ are optionally further substituted with one or more alkylamino, alkyloxy, amino, aminoalkyl, halogen, hydroxyl, hydroxyl with an oxygen protecting group, or protected amino, wherein $X_1$ and $X_2$ are each independently absent, or are —N(alkyl), NH, or oxygen, or wherein $X_2$—$R_9$ together are $N_3$ or are a saturated or unsaturated heterocyclic moiety;

p is 2-10, and $R_9$ is hydrogen, or a $C_1$-$C_{20}$ alkyl($C_3$-$C_{14}$)aryl, $C_1$-$C_{20}$ alkyl($C_3$-$C_{14}$)heteroaryl, $C_3$-$C_{14}$ aryl, $C_3$-$C_{14}$ heteroaryl moiety, or is —(C═O)NHR_{10}, —(C═O)OR_{10}, or —(C═O)R_{10}, wherein each occurrence of $R_{10}$ is independently $C_2$-$C_{20}$ alkenyl, $C_1$-$C_{20}$ alkyl, $C_7$-$C_{20}$ alkynyl, $C_3$-$C_{14}$ aryl, $C_3$-$C_{20}$ cycloalkenyl, $C_3$-$C_{20}$ cycloalkyl, $C_3$-$C_{20}$ cycloalkynyl, $C_2$-$C_{20}$ heteroalkenyl, $C_1$-$C_{20}$ heteroalkyl, $C_2$-$C_{20}$ heteroalkynyl, $C_3$-$C_{14}$ heteroaryl, $C_3$-$C_{20}$ heterocycloalkenyl, $C_3$-$C_{20}$ heterocycloalkyl, $C_3$-$C_{20}$ heterocycloalkynyl, or hydrogen; or $R_9$ is —$SO_2(R_{11})$, wherein $R_{11}$ is a $C_2$-$C_{20}$ alkenyl, $C_1$-$C_{20}$ alkyl, or $C_2$-$C_{20}$ alkynyl moiety, wherein one or more of $R_9$, $R_{10}$, or $R_{11}$ are optionally substituted with one or more alkylamino, alkyloxy, amino, aminoalkyl, halogen, hydroxyl, hydroxyl with an oxygen protecting group, or protected amino;

$R_2$ is $C_2$-$C_{20}$ alkenyl, $C_1$-$C_{20}$ alkyl, $C_2$-$C_{20}$ alkynyl, $C_3$-$C_{14}$ aryl, $C_3$-$C_{20}$ cycloalkenyl, $C_3$-$C_{20}$ cycloalkyl, $C_3$-$C_{20}$ cycloalkynyl, $C_2$-$C_{20}$ heteroalkenyl, $C_1$-$C_{20}$ heteroalkyl, $C_2$-$C_{20}$ heteroalkynyl, $C_3$-$C_{14}$ heteroaryl, $C_3$-$C_{20}$ heterocycloalkenyl, $C_3$-$C_{20}$ heterocycloalkyl, $C_3$-$C_{20}$ heterocycloalkynyl, or hydrogen;

$R_3$ and $R_5$ are each independently halogen or hydrogen;
$R_4$ is halogen, hydrogen, or methyl;
$R_6$ is hydrogen or an oxygen protecting group;
$R_7$ is hydrogen, hydroxyl, or hydroxyl with an oxygen protecting group;

wherein oxygen protecting groups are selected from the group consisting of acetate, benzoate, benzyl ethers, benzyloxymethyl ether, carbonates, cyclic acetals, dichloroacetate, esters, ethyl ethers, formate, ketals, methoxymethyl ether, methylthiomethyl ether, methyl ethers, p-methoxybenzyloxymethyl ether, silyl ethers, t-butyldimethylsilyl ether, t-butyldiphenyl silyl ether, tribenzyl silyl ether, triethylsilylether, trifluoroacetate, triisopropylsilyl ether, and trimethylsilyl ether and wherein nitrogen protecting groups are selected from the group consisting of amides, carbamates, cyclic imides, enamines, imines, N-alkyl amines, N-aryl amines, and Troc; and wherein $C_3$-$C_{14}$ heteroaryl moieties are selected from cyclic aromatic moieties having from five to ten ring atoms of which one ring atom is selected from N, O, and S; zero, one or two ring atoms are additional heteroatoms independently selected from N, O, and S; and the remaining ring atoms are carbon.

In some embodiments, the presently disclosed subject matter is directed to compounds of the general formula (II):

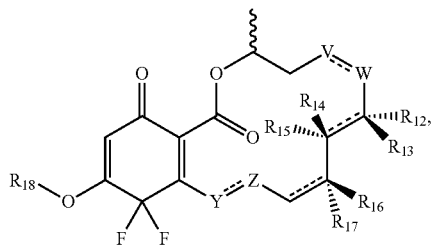

or a pharmaceutically acceptable derivative thereof; wherein

V-----W is $CH_2CH_2$, CH=CH, or

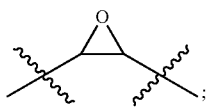 [SMILES: *C1OC1*]

Y-----Z is $CH_2CH_2$,

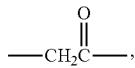

CH=CH, or

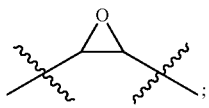 [SMILES: *C1OC1*]

$R_{12}$ is hydrogen, hydroxyl, or methyl;

$R_{13}$, $R_{15}$, and $R_{17}$ may each independently be present or absent and if present $R_{13}$, $R_{15}$, and $R_{17}$ are each independently hydrogen or hydroxyl;

$R_{14}$ and $R_{16}$ are each independently hydrogen or hydroxyl;

wherein $R_{12}$ and $R_{13}$, when taken together, may optionally be =O wherein $R_{13}$ and $R_{14}$, when taken together, may optionally be

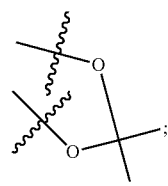

wherein $R_{14}$ and $R_{16}$, when taken together, may optionally be

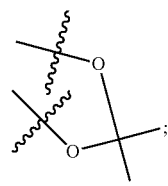 [SMILES: *OC(C)(C)O*]

and $R_{18}$ is $C_1$-$C_{20}$ alkyl, hydrogen, methyl, or

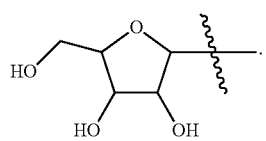 [SMILES: *C1OC(CO)C(O)C1O]

The following structures (or a pharmaceutically acceptable derivative thereof) illustrate several exemplary types of compounds of the presently disclosed subject matter:

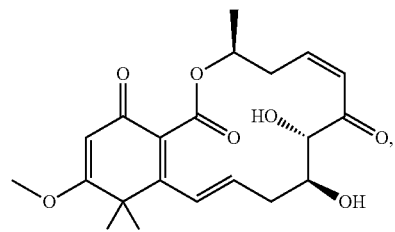

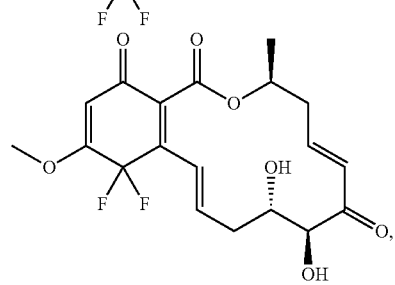

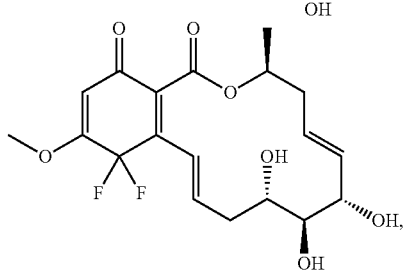

-continued

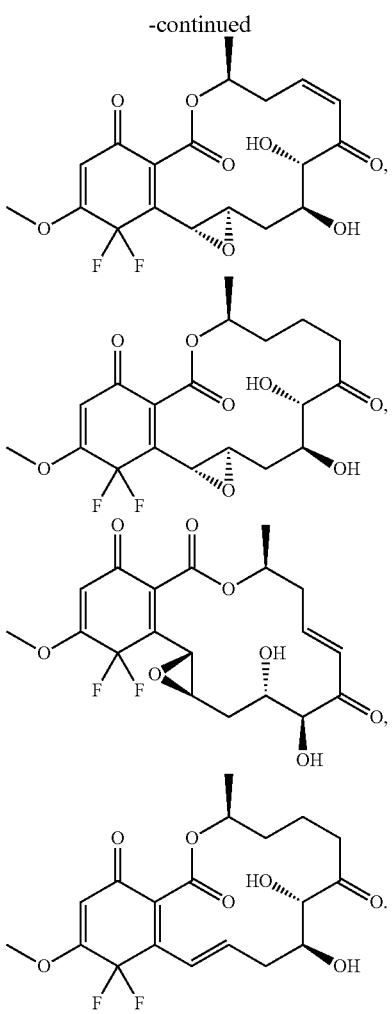

The phrase, "pharmaceutically acceptable derivative", as used herein, denotes any pharmaceutically acceptable salt, ester, or salt of such ester, of such compound, or any other adduct or derivative which, upon administration to a patient, is capable of providing (directly or indirectly) a compound as otherwise described herein, or a metabolite or residue thereof. Pharmaceutically acceptable derivatives thus include among others pro-drugs. A pro-drug is a derivative of a compound, usually with significantly reduced pharmacological activity, which contains an additional moiety, which is susceptible to removal in vivo yielding the parent molecule as the pharmacologically active species. An example of a pro-drug is an ester, which is cleaved in vivo to yield a compound of interest. Pro-drugs of a variety of compounds, and materials and methods for derivatizing the parent compounds to create the pro-drugs, are known and may be adapted to the present invention. Certain exemplary pharmaceutical compositions and pharmaceutically acceptable derivatives will be discussed in more detail herein below.

As used herein throughout, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts of amines, carboxylic acids, and other types of compounds, are well known in the art. For example, S. M. Berge, et al. describe pharmaceutically acceptable salts in detail in J. Pharmaceutical Sciences, 66: 1-19 (1977), incorporated herein by reference. The salts can be prepared in situ during the final isolation and purification of the compounds of the invention, or separately by reacting a free base or free acid function with a suitable reagent, as described generally below. For example, a free base function can be reacted with a suitable acid. Furthermore, where the compounds of the invention carry an acidic moiety, suitable pharmaceutically acceptable salts thereof may, include metal salts such as alkali metal salts, e.g. sodium or potassium salts; and alkaline earth metal salts, e.g. calcium or magnesium salts. Examples of pharmaceutically acceptable, non-toxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Additionally, as used herein, the term "pharmaceutically acceptable ester" refers to esters that hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moeity advantageously has not more than 6 carbon atoms. Examples of particular esters include formates, acetates, propionates, butyrates, acrylates and ethylsuccinates.

Furthermore, the term "pharmaceutically acceptable prodrugs" as used herein refers to those prodrugs of the compounds of the present invention which are, within the scope of sound medical judgment, suitable for use in contact with the issues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

Some of the foregoing compounds can comprise one or more asymmetric centers, and thus can exist in various isomeric forms, e.g., stereoisomers and/or diastereomers. Thus, inventive compounds and pharmaceutical compositions thereof may be in the form of an individual enantiomer, diastereomer or geometric isomer, or may be in the form of a mixture of stereoisomers. In certain embodiments, the compounds of the invention are enantiopure compounds. In certain other embodiments, mixtures of stereoisomers or diastereomers are provided.

Furthermore, certain compounds, as described herein may have one or more double bonds that can exist as either the Z or E isomer, unless otherwise indicated. The invention additionally encompasses the compounds as individual isomers substantially free of other isomers and alternatively, as mixtures of various isomers, e.g., racemic mixtures of stereoisomers. In addition to the above-mentioned compounds per se, this invention also encompasses pharmaceutically acceptable derivatives of these compounds and compositions comprising one or more compounds of the invention and one or more pharmaceutically acceptable excipients or additives.

Compounds of the invention may be prepared by crystallization under different conditions and may exist as one or a combination of polymorphs. For example, different polymorphs may be identified and/or prepared using different solvents, or different mixtures of solvents for recrystallization; by performing crystallizations at different temperatures; or by using various modes of cooling, ranging from very fast to very slow cooling during crystallizations. Polymorphs may also be obtained by heating or melting the compound followed by gradual or fast cooling. The presence of polymorphs may be determined by solid probe NMR spectroscopy, IR spectroscopy, differential scanning calorimetry, powder X-ray diffractogram and/or other techniques. Thus, the present invention encompasses inventive compounds, their derivatives, their tautomeric forms, their stereoisomers, their polymorphs, their pharmaceutically acceptable salts their pharmaceutically acceptable solvates and pharmaceutically acceptable compositions containing them.

The chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in "Organic Chemistry", Thomas Sorrell, University Science Books, Sausalito: 1999, the entire contents of which are incorporated herein by reference.

By the term "protecting group", as used herein, it is meant that a particular functional moiety, e.g., O, S, or N, is temporarily blocked so that a reaction can be carried out selectively at another reactive site in a multifunctional compound. In preferred embodiments, a protecting group reacts selectively in good yield to give a protected substrate that is stable to the projected reactions; the protecting group must be selectively removed in good yield by readily available, preferably nontoxic reagents that do not attack the other functional groups; the protecting group forms an easily separable derivative (more preferably without the generation of new stereogenic centers); and the protecting group has a minimum of additional functionality to avoid further sites of reaction. Oxygen, sulfur, nitrogen and carbon protecting groups may be utilized. Oxygen protecting groups include, but are not limited to methyl ethers, substituted methyl ethers (e.g., MOM (methoxymethyl ether), MTM (methylthiomethyl ether), BOM (benzyloxymethyl ether), PMBM or MPM (p-methoxybenzyloxymethyl ether), to name a few), substituted ethyl ethers, substituted benzyl ethers, silyl ethers (e.g., TMS (trimethylsilyl ether), TES (triethylsilylether), TIPS (triisopropylsilyl ether), TBDMS (t-butyldimethylsilyl ether), tribenzyl silyl ether, TBDPS (t-butyldiphenyl silyl ether), to name a few), esters (e.g., formate, acetate, benzoate (Bz), trifluoroacetate, dichloroacetate, to name a few), carbonates, cyclic acetals and ketals. Nitrogen protecting groups include, but are not limited to, carbamates (including methyl, ethyl and substituted ethyl carbamates (e.g., Troc), to name a few) amides, cyclic imide derivatives, N-Alkyl and N-Aryl amines, imine derivatives, and enamine derivatives, to name a few. The present invention is not intended to be limited to these protecting groups; rather, a variety of additional equivalent protecting groups can be readily identified using the above criteria and utilized in the present invention. Additionally, a variety of protecting groups are described in "Protective Groups in Organic Synthesis" Third Ed. Greene, T. W. and Wuts, P. G., Eds., John Wiley & Sons, New York: 1999, the entire contents of which are hereby incorporated by reference.

It will be appreciated that the compounds, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in the treatment, for example of inflammatory and proliferative disorders, including, but not limited to rheumatoid arthritis, psoriasis, asthma and cancer. The term "stable", as used herein, preferably refers to compounds which possess stability sufficient to allow manufacture and which maintain the integrity of the compound for a sufficient period of time to be detected and preferably for a sufficient period of time to be useful for the purposes detailed herein.

The term "aliphatic", as used herein, includes both saturated and unsaturated, straight chain (i.e., unbranched) or branched aliphatic hydrocarbons, which are optionally substituted with one or more functional groups. As will be appreciated by one of ordinary skill in the art, "aliphatic" is intended herein to include, but is not limited to, alkyl, alkenyl, alkynyl moieties. Thus, as used herein, the term "alkyl" includes straight and branched alkyl groups. An analogous convention applies to other generic terms such as "alkenyl", "alkynyl" and the like. Furthermore, as used herein, the terms "alkyl", "alkenyl", "alkynyl" and the like encompass both substituted and unsubstituted groups. In certain embodiments, as used herein, "lower alkyl" is used to indicate those alkyl groups (cyclic, acyclic, substituted, unsubstituted, branched or unbranched) having 1-6 carbon atoms.

In certain embodiments, the alkyl, alkenyl and alkynyl groups employed in the invention contain 1-20 aliphatic carbon atoms. In certain other embodiments, the alkyl, alkenyl, and alkynyl groups employed in the invention contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups employed in the invention contain 1-6 aliphatic carbon atoms. In yet other embodiments, the alkyl, alkenyl, and alkynyl groups employed in the invention contain 1-4 carbon atoms. Illustrative aliphatic groups thus include, but are not limited to, for example, methyl, ethyl, n-propyl, isopropyl, allyl, n-butyl, sec-butyl, isobutyl, tert-butyl, n-pentyl, sec-pentyl, isopentyl, tert-pentyl, n-hexyl, sec-hexyl, moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl(propargy 1), 1-propynyl and the like.

The term "alicyclic", as used herein, refers to compounds which combine the properties of aliphatic and cyclic compounds and include but are not limited to cyclic, or polycyclic aliphatic hydrocarbons and bridged cycloalkyl compounds, which are optionally substituted with one or more functional groups. As will be appreciated by one of ordinary skill in the art, "alicyclic" is intended herein to include, but is not limited to, cycloalkyl, cycloalkenyl, and cycloalkynyl moieties, which are optionally substituted with one or more functional groups. Illustrative alicyclic groups thus include, but are not limited to, for example, cyclopropyl, —CH$_2$-cyclopropyl, cyclobutyl, —CH$_2$-cyclobutyl, cyclopentyl, —CH$_2$-cyclopentyl-n, cyclohexyl, —CH$_2$-cyclohexyl, cyclohexenylethyl, cyclohexanylethyl, norborbyl moieties and the like, which again, may bear one or more substituents.

The term "alkoxy" (or "alkyloxy"), or "thioalkyl" as used herein refers to an alkyl group, as previously defined, attached to the parent molecular moiety through an oxygen atom or through a sulfur atom. In certain embodiments, the alkyl group contains 1-20 aliphatic carbon atoms. In certain other embodiments, the alkyl group contains 1-10 aliphatic carbon atoms. In yet other embodiments, the alkyl, alkenyl, and alkynyl groups employed in the invention contain 1-8 aliphatic carbon atoms. In still other embodiments, the alkyl group contains 1-6 aliphatic carbon atoms. In yet other embodiments, the alkyl group contains 1-4 aliphatic carbon atoms. Examples of alkoxy, include but are not limited to, methoxy, ethoxy, propoxy, isopropoxy, n-butoxy, tert-butoxy, neopentoxy and n-hexoxy. Examples of thioalkyl include, but are not limited to, methylthio, ethylthio, propylthio, isopropylthio, n-butylthio, and the like.

The term "alkylamino" refers to a group having the structure —NHR' wherein R' is alkyl, as defined herein. The term "aminoalkyl" refers to a group having the structure NH$_2$R'—, wherein R' is alkyl, as defined herein. In certain embodiments, the alkyl group contains 1-20 aliphatic carbon atoms. In certain other embodiments, the alkyl group contains 1-10 aliphatic carbon atoms. In yet other embodiments, the alkyl, alkenyl, and alkynyl groups employed in the invention contain 1-8 aliphatic carbon atoms. In still other embodiments, the alkyl group contains 1-6 aliphatic carbon atoms. In yet other embodiments, the alkyl group contains 1-4 aliphatic carbon atoms. Examples of alkylamino include, but are not limited to, methylamino, ethylamino, iso-propylamino and the like.

Some examples of substituents of the above-described aliphatic (and other) moieties of compounds of the invention include, but are not limited to aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, heteroaliphatic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments described herein.

In general, the terms "aryl" and "heteroaryl", as used herein, refer to stable mono- or polycyclic, heterocyclic, polycyclic, and polyheterocyclic unsaturated moieties having preferably 3-14 carbon atoms, each of which may be substituted or unsubstituted. It will also be appreciated that aryl and heteroaryl moieties, as defined herein may be attached via an aliphatic, alicyclic, heteroaliphatic, heteroalicyclic, alkyl or heteroalkyl moiety and thus also include -(aliphatic)aryl, -(heteroaliphatic)aryl, -(aliphatic) heteroaryl, -(heteroaliphatic)heteroaryl, -(alkyl)aryl, -(heteroalkyl)aryl, -(heteroalkyl)aryl, and -(heteroalkyl)heteroaryl moieties. Thus, as used herein, the phrases "aryl or heteroaryl" and "aryl, heteroaryl, -(aliphatic)aryl, -(heteroaliphatic)aryl, -(aliphatic)heteroaryl, -(heteroaliphatic)heteroaryl, -(alkyl)aryl, -(heteroalkyl)aryl, (heteroalkyl)aryl, and -(heteroalkyl)heteroaryl" are interchangeable. Substituents include, but are not limited to, any of the previously mentioned substitutents, i.e., the substituents recited for aliphatic moieties, or for other moieties as disclosed herein, resulting in the formation of a stable compound. In certain embodiments of the present invention, "aryl" refers to a mono- or bicyclic carbocyclic ring system having one or two aromatic rings including, but not limited to, phenyl, naphthyl, tetrahydronaphthyl, indanyl, indenyl and the like. In certain embodiments of the present invention, the term "heteroaryl", as used herein, refers to a cyclic aromatic radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will be appreciated that aryl and heteroaryl groups (including bicyclic aryl groups) can be unsubstituted or substituted, wherein substitution includes replacement of one, two or three of the hydrogen atoms thereon independently with any one or more of the following moieties including, but not limited to: aliphatic; heteroaliphatic; aryl;

heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, heteroaliphatic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments described herein.

The term "cycloalkyl", as used herein, refers specifically to groups having three to seven, preferably three to ten carbon atoms. Suitable cycloalkyls include, but are not limited to cyclopropyl, cyclobutyl, cyclopentyl, cyclohexyl, cycloheptyl and the like, which, as in the case of aliphatic, heteroaliphatic or heterocyclic moieties, may optionally be substituted with substituents including, but not limited to aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, heteroaliphatic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments described herein.

The term "heteroaliphatic", as used herein, refers to aliphatic moieties in which one or more carbon atoms in the main chain have been substituted with a heteroatom. Thus, a heteroaliphatic group refers to an aliphatic chain which contains one or more oxygen, sulfur, nitrogen, phosphorus or silicon atoms, e.g., in place of carbon atoms. Heteroaliphatic moieties may be branched or linear unbranched. In certain embodiments, heteroaliphatic moieties are substituted by independent replacement of one or more of the hydrogen atoms thereon with one or more moieties including, but not limited to aliphatic; alicyclic; heteroaliphatic; heteroalicyclic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, alicyclic, heteroaliphatic, heteroalicyclic, aryl, heteroaryl, alkylaryl, or alkylheteroaryl, wherein any of the aliphatic, alicyclic, heteroaliphatic, heteroalicyclic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments described herein.

The term "heteroalicyclic", as used herein, refers to compounds which combine the properties of heteroaliphatic and cyclic compounds and include but are not limited to saturated and unsaturated mono- or polycyclic heterocycles such as morpholino, pyrrolidinyl, furanyl, thiofuranyl, pyrrolyl etc., which are optionally substituted with one or more functional groups, as defined herein.

Additionally, it will be appreciated that any of the alicyclic or heteroalicyclic moieties described above and herein may comprise an aryl or heteroaryl moiety fused thereto. Additional examples of generally applicable substituents are illustrated by the specific embodiments described herein.

The terms "halo" and "halogen" as used herein refer to an atom selected from fluorine, chlorine, bromine and iodine.

The term "haloalkyl" denotes an alkyl group, as defined above, having one, two, or three halogen atoms attached thereto and is exemplified by such groups as chloromethyl, bromoethyl, trifluoromethyl, and the like.

The term "heterocycloalkyl" or "heterocycle", as used herein, refers to a non-aromatic 5-, 6- or 7-membered ring or a polycyclic group, including, but not limited to a bi- or tri-cyclic group comprising fused six-membered rings having between one and three heteroatoms independently selected from oxygen, sulfur and nitrogen, wherein (i) each 5-membered ring has 0 to 1 double bonds and each 6-membered ring has 0 to 2 double bonds, (ii) the nitrogen and sulfur heteroatoms may be optionally be oxidized, (iii) the nitrogen heteroatom may optionally be quaternized, and (iv) any of the above heterocyclic rings may be fused to an aryl or heteroaryl ring. Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl. In certain embodiments, a "substituted heterocycloalkyl or heterocycle" group is utilized and as used herein, refers to a heterocycloalkyl or heterocycle group, as defined above, substituted by the independent replacement of one, two or three of the hydrogen atoms thereon with but are not limited to aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, heteroaliphatic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substitutents described above and herein may be substituted or unsubstituted. Additional examples or generally applicable substituents are illustrated by the specific embodiments described herein.

As used herein, the terms "aliphatic", "heteroaliphatic", "alkyl", "alkenyl", "alkynyl", "heteroalkyl", "heteroalkenyl", "heteroalkynyl", and the like encompass substituted and unsubstituted, saturated and unsaturated, and linear and branched groups. Similarly, the terms "alicyclic", "heteroalicyclic", "heterocycloalkyl", "heterocycle" and the like encompass substituted and unsubstituted, and saturated and unsaturated groups. Additionally, the terms "cycloalkyl", "cycloalkenyl", "cycloalkynyl", "heterocycloalkyl", "heterocycloalkenyl", "heterocycloalkynyl", "aryl", "heteroaryl" and the like encompass both substituted and unsubstituted groups.

II. Compositions

In some embodiments, the presently disclosed subject matter provides pharmaceutical compositions comprising the compounds of formula (I). In other embodiments, the compound is present in an amount effective to inhibit MAP3K. In other embodiments, the compound is present in an amount effective to inhibit TAK-1. In some embodiments, the presently disclosed subject matter provides pharmaceutical compositions comprising the compounds of formula (II). In other embodiments, the compound is present in an amount effective to inhibit MAP3K. In other embodiments, the compound is present in an amount effective to inhibit TAK-1.

TAK-1 is a member of the serine/threonine mitogen-activated protein kinase (MAP3K) family.[3] A wide range of extracellular stimuli, such as proinflammatory interleukins, activate the intracellular TAK-1 via membrane-bound receptors.[4] Activation of upstream key signaling enzyme results in subsequent activation of specific MAP2Ks and MAPKs. This cascade of downstream activation, via phosphorylation, leads to activation of a number of transcription factors including AP-1 and NF-κB[5] which are known to regulate inflammatory responses and apoptosis. Inhibition of upstream kinases such as MAP3Ks has an advantage over inhibiting downstream signaling molecules, mostly due to the former being more stimuli-specific.[6] It has been shown, indeed, that inhibiting TAK-1/NF-κB signaling pathway, using either TAK-1 inhibitors or via silencing of TAK-1 expression, promotes apoptosis in colon cancer,[7] suppresses renal cell carcinoma survival,[8] proliferation of LPS-induced human hepatocellular carcinoma[9] and reverses chemoresistance of pancreatic cancer.[10] TAK-1 is up-regulated in hepatocellular carcinoma[9, 26], renal cell carcinoma[8], breast cancer[27, 28], head and neck squamous cell carcinoma[29], pancreatic cancer[10, 30], lung cancer[31, 32], colon cancer[7], leukemia[33], and ovarian cancer[34]. As such, the inventive compounds, and pharmaceutical compositions thereof, are useful for the treatment of or reducing the likelihood of hepatocellular carcinoma, renal cell carcinoma, breast cancer, head and neck squamous cell carcinoma, pancreatic cancer, lung cancer, colon cancer, leukemia, and ovarian cancer.

The pharmaceutical compositions of the present invention additionally comprise a pharmaceutically acceptable carrier, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutical compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatine; talc; excipients such as cocoa butter and suppository waxes; oils such as peanut oil, cottonseed oil; safflower oil, sesame oil; olive oil; corn oil and soybean oil; glycols; such as propylene glycol; esters such as ethyl oleate and ethyl laurate; agar; buffering agents such as magnesium hydroxide and aluminum hydroxide; alginic acid; pyrogenfree water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

In certain embodiments, these compositions optionally further comprise one or more additional therapeutic agents. Alternatively, a compound of this invention may be administered to a patient in need thereof in combination with the administration of one or more other therapeutic agents. For example, additional therapeutic agents for conjoint administration or inclusion in a pharmaceutical composition with a compound of this invention may be an immunomodulatory agent (e.g., an agent for the treatment of, rheumatoid arthritis, psoriasis, multiple sclerosis, or asthma) or antiangiogenesis agent or anticancer agent approved for the treatment of cancer, as discussed in more detail herein, or it may be any one of a number of agents undergoing approval in the Food and Drug Administration that ultimately obtain approval for the treatment of an immune disorder or cancer. It will also be appreciated that certain of the compounds of present invention can exist in free form for treatment, or where appropriate, as a pharmaceutically acceptable derivative thereof.

It will be appreciated that the inventive compound may be administered systemically in dosage forms, formulations or e.g. suitable delivery devices or implants containing conventional, non-toxic pharmaceutically acceptable carriers and adjuvants such that the compound effectiveness is optimized. For example, the inventive compound may be formulated together with appropriate excipients into a pharmaceutical composition, which, upon administration of the composition to the subject, systemically releases the active substance in a controlled manner. Alternatively, or additionally, compound dosage form designs may be optimized so as to increase the compound effectiveness upon administration. The above strategies (i.e., dosage form design and rate control of drug input), when used alone or in combination, can result in a significant increase in compound effectiveness and are considered part of the invention.

According to the present invention, compounds of the present invention may be assayed in any of the available assays known in the art for identifying compounds having antiangiogenic activity, anti-inflammatory activity, protein kinase inhibitory activity, NF-κB activation inhibitory activity and AP-1 activation inhibitory activity. For example, the assay may be cellular or non-cellular, in vivo or in vitro, high- or low-throughput format, etc.

Thus, in one aspect, compounds of this invention which are of particular interest include those which: exhibit activity as inhibitors of NF-κB activation, AP-1 activation and protein kinases (e.g., MAP3K, TAK-1, MEKK1, MEK1, VEGFr, PDGFr); exhibit activity as inhibitors of production of pro-inflammatory and/or immunologic cytokines (e.g., TNFα, IL-1, IL-6, IL-8, IL-2); exhibit an antiproliferative or an antiangiogenic effect on solid tumors; exhibit an anti-inflammatory effect on suitable cell lines maintained in vitro, or in animal studies using a scientifically acceptable model; are useful for the treatment of photoaging-related disorders/conditions; and/or exhibit a favorable therapeutic profile (e.g., safety, efficacy, and stability). The identification of NF-κB as a key player in the pathogenesis of inflammation suggest that NF-κB targeted therapeutics may be effective in inflammatory and immune disorders (see, generally, NF-κB in Defense and Disease, J. Clin. Investig. 2001, 107, 7). Furthermore, certain compounds of the invention inhibit receptor tyrosine kinase activity such as VEGFr and PDGFr in vitro, and are useful for the treatment of cancer, including solid tumors (see, Angiogenesis: Potentials for Pharmacologic Intervention in the Treatment of Cancer, Cardiovascular Diseases, and Chronic Inflammation, Pharmacological Reviews, 2000, 52, 237). Certain of the compounds as described herein exhibit activity generally as inhibitors of NF-κB activation, AP-1 activation and protein kinases (e.g., MAP3K, TAK-1, MEKK1, MEK1, VEGFr, PDGFr). Certain compounds of the invention demonstrate immunosuppressive activity, or inhibit tumor growth and angiogenesis.

In assays to determine the ability of compounds to inhibit MAP3K, certain inventive compounds exhibited $IC_{50}$ values less than 10 µM. In certain other embodiments, inventive compounds exhibit $IC_{50}$ values less than 7.5 µM. In certain embodiments, inventive compounds exhibit $IC_{50}$ values less than 5 µM. In certain other embodiments, inventive compounds exhibit $IC_{50}$ values less than 2.5 µM. In certain embodiments, inventive compounds exhibit $IC_{50}$ values less than 1 µM. In certain embodiments, inventive compounds exhibit $IC_{50}$ values less than 0.75 µM. In certain embodiments, inventive compounds exhibit $IC_{50}$ values less than 0.5 µM. In certain embodiments, inventive compounds exhibit $IC_{50}$ values less than 0.25 µM. In certain embodiments, inventive compounds exhibit $IC_{50}$ values less than 0.1 µM. In certain other embodiments, inventive compounds exhibit $IC_{50}$ values less than 75 nM. In certain other embodiments, inventive compounds exhibit $IC_{50}$ values less than 50 nM. In certain other embodiments, inventive compounds exhibit $IC_{50}$ values less than 25 nM. In certain other embodiments, inventive compounds exhibit $IC_{50}$ values less than 10 nM. In other embodiments, exemplary compounds exhibit $IC_{50}$ values less than 7.5 nM. In other embodiments, exemplary compounds exhibit $IC_{50}$ values less than 5 nM.

In assays to determine the ability of compounds to inhibit TAK-1, certain inventive compounds exhibited $IC_{50}$ values less than 10 µM. In certain other embodiments, inventive compounds exhibit $IC_{50}$ values less than 7.5 µM. In certain embodiments, inventive compounds exhibit $IC_{50}$ values less than 5 µM. In certain other embodiments, inventive compounds exhibit $IC_{50}$ values less than 2.5 µM. In certain embodiments, inventive compounds exhibit $IC_{50}$ values less than 1 µM. In certain embodiments, inventive compounds exhibit $IC_{50}$ values less than 0.75 µM. In certain embodiments, inventive compounds exhibit $IC_{50}$ values less than 0.5 µM. In certain embodiments, inventive compounds exhibit $IC_{50}$ values less than 0.25 µM. In certain embodiments, inventive compounds exhibit $IC_{50}$ values less than 0.1 µM. In certain other embodiments, inventive compounds exhibit $IC_{50}$ values less than 75 nM. In certain other embodiments, inventive compounds exhibit $IC_{50}$ values less than 50 nM. In certain other embodiments, inventive compounds exhibit $IC_{50}$ values less than 25 nM. In certain other embodiments, inventive compounds exhibit $IC_{50}$ values less than 10 nM. In other embodiments, exemplary compounds exhibit $IC_{50}$ values less than 7.5 nM. In other embodiments, exemplary compounds exhibit $IC_{50}$ values less than 5 nM.

In assays to determine the ability of compounds to inhibit NF-κB, certain inventive compounds exhibited $IC_{50}$ values less than 10 µM. In certain other embodiments, inventive compounds exhibit $IC_{50}$ values less than 7.5 µM. In certain embodiments, inventive compounds exhibit $IC_{50}$ values less than 5 µM. In certain other embodiments, inventive compounds exhibit $IC_{50}$ values less than 2.5 µM. In certain embodiments, inventive compounds exhibit $IC_{50}$ values less than 1 µM. In certain embodiments, inventive compounds exhibit $IC_{50}$ values less than 0.75 µM. In certain embodiments, inventive compounds exhibit $IC_{50}$ values less than 0.5 µM. In certain embodiments, inventive compounds exhibit $IC_{50}$ values less than 0.25 µM. In certain embodiments, inventive compounds exhibit $IC_{50}$ values less than 0.1 µM. In certain other embodiments, inventive compounds exhibit $IC_{50}$ values less than 75 nM. In certain other embodiments, inventive compounds exhibit $IC_{50}$ values less than 50 nM. In certain other embodiments, inventive compounds exhibit $IC_{50}$ values less than 25 nM. In certain other embodiments, inventive compounds exhibit $IC_{50}$ values less than 10 nM. In other embodiments, exemplary compounds exhibit $IC_{50}$ values less than 7.5 nM. In other embodiments, exemplary compounds exhibit $IC_{50}$ values less than 5 nM.

In still other embodiments, certain compounds may be tested for their ability to inhibit the growth of cancer cell lines in vitro. Certain of these compounds exhibited $IC_{50}$ values less than 10 µM. In certain other embodiments, inventive compounds exhibit $IC_{50}$ values less than 7.5 µM. In certain embodiments, inventive compounds exhibit $IC_{50}$ values less than 5 µM. In certain other embodiments, inventive compounds exhibit $IC_{50}$ values less than 2.5 µM. In certain embodiments, inventive compounds exhibit $IC_{50}$ values less than 1 µM. In certain embodiments, inventive compounds exhibit $IC_{50}$ values less than 0.75 µM. In certain embodiments, inventive compounds exhibit $IC_{50}$ values less than 0.5 µM. In certain embodiments, inventive compounds exhibit $IC_{50}$ values less than 0.25 µM. In certain embodiments, inventive compounds exhibit $IC_{50}$ values less than 0.1 µM. In certain other embodiments, inventive compounds exhibit $IC_{50}$ values less than 75 nM. In certain other embodiments, inventive compounds exhibit $IC_{50}$ values less than 50 nM. In certain other embodiments, inventive compounds exhibit $IC_{50}$ values less than 25 nM. In certain other embodiments, inventive compounds exhibit $IC_{50}$ values less than 10 nM. In other embodiments, exemplary compounds exhibit $IC_{50}$ values less than 7.5 nM. In other embodiments, exemplary compounds exhibit $IC_{50}$ values less than 5 nM.

In still other embodiments, certain compounds may be tested for their ability to inhibit the growth of ovarian cancer cell lines in vitro. Certain of these compounds exhibited $IC_{50}$ values less than 10 µM. In certain other embodiments, inventive compounds exhibit $IC_{50}$ values less than 7.5 µM. In certain embodiments, inventive compounds exhibit $IC_{50}$ values less than 5 µM. In certain other embodiments, inventive compounds exhibit $IC_{50}$ values less than 2.5 µM. In certain embodiments, inventive compounds exhibit $IC_{50}$ values less than 1 µM. In certain embodiments, inventive compounds exhibit $IC_{50}$ values less than 0.75 µM. In certain embodiments, inventive compounds exhibit $IC_{50}$ values less than 0.5 µM. In certain embodiments, inventive compounds exhibit $IC_{50}$ values less than 0.25 µM. In certain embodiments, inventive compounds exhibit $IC_{50}$ values less than 0.1 µM. In certain other embodiments, inventive compounds exhibit $IC_{50}$ values less than 75 nM. In certain other embodiments, inventive compounds exhibit $IC_{50}$ values less than 50 nM. In certain embodiments, inventive compounds exhibit $IC_{50}$ values less than 25 nM. In certain other embodiments, inventive compounds exhibit $IC_{50}$ values less than 10 nM. In other embodiments, exemplary compounds exhibit $IC_{50}$ values less than 7.5 nM. In other embodiments, exemplary compounds exhibit $IC_{50}$ values less than 5 nM.

Certain compounds of the invention exhibit immunomodulatory activity and may exhibit activity for the inhibition of angiogenesis through inhibition of receptor tyrosine kinases. As such, the inventive compounds, and pharmaceutical compositions thereof, are useful for the treatment or prevention of a variety of disorders, including, but not limited to, sepsis, glomerulonephropathy, rheumatoid arthritis (including ankylosing spondylitis), psoriatic arthritis, osteoarthritis, osteoporosis, allergic rhinitis, ocular inflammation, inflammatory bowel disease, atopic dermatitis, psoriasis, asthma, Crohn's disease, ulcerative colitis, inflammatory pulmonary disease, hepatitis, autoimmune disorders, diabetes, AIDS, solid tumor cancers, Leukemia, lymphomas, non-hodgkin's B-cell lymphomas, chronical lymphocytic leukemia (CLL), multiple myeloma, systemic lupus erythematosus, allograft rejection/graft versus host disease, eczema, uticaria, myasthenia gravis, idiopathic thrombocytopenia purpura, cardiovascular disease (e.g., myocardial infarction, atherosclerosis), hepatitis, productive nephritis, adenovirus, diseases/disorders of the central nervous system (stroke, Alzheimer's disease, epilepsy), and for the treatment of the symptoms of malaria, to name a few. In certain embodiments, compounds of the invention, and pharmaceutical compositions thereof, are particularly useful for the treatment of rheumatoid arthritis, psoriasis, multiple sclerosis, asthma and cancer.

III. Methods of Treatment

In some embodiments, the presently disclosed subject matter provides a method for use of the compounds of formula (I), in the treatment of various disorders as described herein, comprising administering to a subject in need thereof a therapeutically effective amount of a compound of formula (I), and a pharmaceutically acceptable carrier or diluent. In certain embodiments, the present disclosed subject matter provides a method for treating cancer comprising administering to a subject in need thereof a therapeutically effective amount of a compound of Formula (I), and a pharmaceutically acceptable carrier or diluent. In some embodiments, the cancer is hepatocellular carcinoma, renal cell carcinoma, breast cancer, head and neck squamous cell carcinoma, pancreatic cancer, lung cancer, colon cancer, leukemia, or ovarian cancer. In some embodiments, the presently disclosed subject matter provides a method for use of the compounds of formula (II) in the treatment of various disorders as described herein, comprising administering to a subject in need thereof a therapeutically effective amount of a compound of formula (II), and a pharmaceutically acceptable carrier or diluent. In certain embodiments, the present disclosed subject matter provides a method for treating cancer comprising administering to a subject in need thereof a therapeutically effective amount of a compound of Formula (II), and a pharmaceutically acceptable carrier or diluent. In some embodiments, the cancer is hepatocellular carcinoma, renal cell carcinoma, breast cancer, head and neck squamous cell carcinoma, pancreatic cancer, lung cancer, colon cancer, leukemia, or ovarian cancer.

The method involves the administration of a therapeutically effective amount of the compound or pharmaceutically acceptable derivative thereof to a subject (including, but not limited to a human or animal) in need of it. As used herein, "therapeutically effective amount" or an "effective amount" indicates an amount that results in a desired pharmacological and/or physiological effect for the condition. The effect may be prophylactic in terms of completely or partially preventing a condition or symptom thereof and/or may be therapeutic in terms of a partial or complete cure for the condition and/or adverse effect attributable to the condition. The exact amount required will vary from subject to subject, depending on the species, age, and general condition of the subject, the severity of the diseases, the particular anticancer agent, its mode of administration, and the like. The compounds of the invention are preferably formulated in dosage unit form for ease of administration and uniformity of dosage. The expression "dosage unit form" as used herein refers to a physically discrete unit of therapeutic agent appropriate for the patient to be treated. It will be understood, however, that the total daily usage of the compounds and compositions of the present invention will be decided by the attending physician within the scope of sound medical judgment. The specific therapeutically effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts (see, for example, Goodman and Gilman's, "The Pharmacological Basis of Therapeutics", Tenth Edition, A. Gilman, J. Hardman and L. Limbird, eds., McGraw-Hill Press, 155-173, 2001, which is incorporated herein by reference in its entirety).

This invention provides novel compounds with a range of biological properties. Compounds of this invention have biological activities relevant for the treatment of inflammatory and immune disorders, photoaging and cancer. In certain embodiments, the compounds of the invention, and pharmaceutical compositions thereof, are useful for the treatment of or reducing the likelihood of hepatocellular carcinoma, renal cell carcinoma, breast cancer, head and neck squamous cell carcinoma, pancreatic cancer, lung cancer, colon cancer, leukemia, ovarian cancer, rheumatoid arthritis, psoriasis, Multiple sclerosis, or asthma. In certain other embodiments, the inventive compounds, and pharmaceutical compositions thereof, also find use in the prevention of restenosis of blood vessels subject to traumas such as angioplasty and stenting.

In certain embodiments, the inventive compounds, and pharmaceutical compositions thereof, are useful for the treatment of an inflammatory disorder or autoimmune disorders. In certain embodiments, the inventive compounds, and pharmaceutical compositions thereof, are useful for the treatment of sepsis, glomerulonephropathy, rheumatoid arthritis (including ankylosing spondylitis), psoriatic arthritis, osteoarthritis, osteoporosis, allergic rhinitis, ocular inflammation, inflammatory bowel disease (Crohn's disease and ulcerative colitis), multiple sclerosis, atopic dermatitis, psoriasis, asthma, inflammatory pulmonary disease, hepatitis, autoimmune disorders, systemic lupus erthematosus, allograft rejection/graft versus host disease, diabetes, AIDS, solid tumor cancers, leukemia, lymphomas, non-hodgkin's B-cell lymphomas, chronical lymphocytic leukemia (CLL), multiple myeloma, eczema, urticaria, myasthenia gravis, idiopathic thrombocytopenia purpura, cardiovascular disease (e.g., myocardial infarction, atherosclerosis), hepatitis, glomerulonephropathy, productive nephritis, adenovirus, diseases/disorders of the central nervous system (e.g., stroke, Alzheimer's disease, epilepsy) and for the treatment of the symptoms of malaria, to name a few.

In certain other embodiments, compounds of the invention are useful for reducing photodamage, and thus, the invention further provides a method for treating photoaging-related disorders/conditions. In certain exemplary embodiments, compounds of the invention are useful for the treatment and/or prevention of skin coarseness, wrinkling, mottled pigmentation, sallowness, laxity, telangiectasia, lentigines, purpura and easy bruising, atrophy, fibrotic depigmented areas, and ultimately premalignant and malignant neoplasms. In certain other exemplary embodiments, compounds of the invention are useful for the treatment and/or prevention of wrinkles and/or skin cancer. The inventive compounds also find use in the prevention of restenosis of blood vessels subject to traumas such as angioplasty and stenting.

Furthermore, after formulation with an appropriate pharmaceutically acceptable carrier or diluent in a desired dosage, the pharmaceutical compositions of this invention can be administered to humans and other animals orally, rectally, parenterally, intracisternally, intravaginally, intraperitoneally, topically (as by powders, ointments, creams or drops), bucally, as an oral or nasal spray, or the like, depending on the severity of the infection being treated. In certain embodiments, the compounds of the invention may be administered at dosage levels of about 0.001 mg/kg to about 50 mg/kg, from about 0.01 mg/kg to about 25 mg/kg, or from about 0.1 mg/kg to about 10 mg/kg of subject body weight per day, one or more times a day, to obtain the desired therapeutic effect. It will also be appreciated that dosages smaller than 0.001 mg/kg or greater than 50 mg/kg (for example 50-100 mg/kg) can be administered to a subject. In certain embodiments, compounds are administered orally or parenterally.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension or crystalline or amorphous material with poor water solubility. The rate of absorption of the drug then depends upon its rate of dissolution that, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include (poly(orthoesters) and poly(anhydrides). Depot injectable formulations are also prepared by entrapping the drug in liposomes or microemulsions, which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose and starch. Such dosage forms may also comprise, as in normal practice, additional substances other than inert diluents, e.g., tableting lubricants and other tableting aids such as magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions, which can be used, include polymeric substances and waxes.

The present invention encompasses pharmaceutically acceptable topical formulations of inventive compounds. The term "pharmaceutically acceptable topical formulation", as used herein, means any formulation which is pharmaceutically acceptable for intradermal administration of a compound of the invention by application of the formulation to the epidermis. In certain embodiments of the invention, the topical formulation comprises a carrier system. Pharmaceutically effective carriers include, but are not limited to, solvents (e.g., alcohols, poly alcohols, water), creams, lotions, ointments, oils, plasters, liposomes, powders, emulsions, microemulsions, and buffered solutions (e.g., hypotonic or buffered saline) or any other carrier known in the art for topically administering pharmaceuticals. A more complete listing of art-known carriers is provided by reference texts that are standard in the art, for example, Remington's Pharmaceutical Sciences, 16th Edition, 1980 and 17th Edition, 1985, both published by Mack Publishing Company, Easton, Pa., the disclosures of which are incorporated herein by reference in their entireties. In certain other embodiments, the topical formulations of the invention may comprise excipients. Any pharmaceutically acceptable excipient known in the art may be used to prepare the inventive pharmaceutically acceptable topical formulations. Examples of excipients that can be included in the topical formulations of the invention include, but are not limited to, preservatives, antioxidants, moisturizers, emollients, buffering agents, solubilizing agents, other penetration agents, skin protectants, surfactants, and propellants, and/or additional therapeutic agents used in combination to the inventive compound. Suitable preservatives include, but are not limited to, alcohols, quaternary amines, organic acids, parabens, and phenols. Suitable antioxidants include, but are not limited to, ascorbic acid and its esters, sodium bisulfite, butylated hydroxytoluene, butylated hydroxyanisole, tocopherols, and chelating agents like EDTA and citric acid. Suitable moisturizers include, but are not limited to, glycerine, sorbitol, polyethylene glycols, urea, and propylene glycol. Suitable buffering agents for use with the invention include, but are not limited to, citric, hydrochloric, and lactic acid buffers. Suitable solubilizing agents include, but are not limited to, quaternary ammonium chlorides, cyclodextrins, benzyl benzoate, lecithin, and polysorbates. Suitable skin protectants that can be used in the topical formulations of the invention include, but are not limited to, vitamin E oil, allatoin, dimethicone, glycerin, petrolatum, and zinc oxide.

In certain embodiments, the pharmaceutically acceptable topical formulations of the invention comprise at least a compound of the invention and a penetration enhancing agent. The choice of topical formulation will depend or several factors, including the condition to be treated, the physicochemical characteristics of the inventive compound and other excipients present, their stability in the formulation, available manufacturing equipment, and costs constraints. As used herein the term "penetration enhancing agent" means an agent capable of transporting a pharmacologically active compound through the stratum corneum and into the epidermis or dermis, preferably, with little or no systemic absorption. A wide variety of compounds have been evaluated as to their effectiveness in enhancing the rate of penetration of drugs through the skin. See, for example, Percutaneous Penetration Enhancers, Maibach H. I. and Smith H. E. (eds.), CRC Press, Inc., Boca Raton, Fla. (1995), which surveys the use and testing of various skin penetration enhancers, and Buyuktimkin et al., Chemical Means of Transdermal Drug Permeation Enhancement in Transdermal and Topical Drug Delivery Systems, Gosh T. K., Pfister W. R., Yum S. I. (Eds.), Interpharm Press Inc., Buffalo Grove, Ill. (1997). In certain exemplary embodiments, penetration agents for use with the invention include, but are not limited to, triglycerides (e.g., soybean oil), aloe compositions (e.g., aloe-vera gel), ethyl alcohol, isopropyl alcohol, octolyphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate) and N-methyl pyrrolidone.

In certain embodiments, the compositions may be in the form of ointments, pastes, creams, lotions, gels, powders, solutions, sprays, inhalants or patches. In certain exemplary embodiments, formulations of the compositions according to the invention are creams, which may further contain saturated or unsaturated fatty acids such as stearic acid, palmitic acid, oleic acid, palmito-oleic acid, cetyl or oleyl alcohols, stearic acid being particularly preferred. Creams of the invention may also contain a non-ionic surfactant, for example, polyoxy-40-stearate. In certain embodiments, the active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms are made by dissolving or dispensing the compound in the proper medium. As discussed above, penetration enhancing agents can also be used to increase the flux of the compound across the skin. The rate can be controlled by either providing a rate controlling membrane or by dispersing the compound in a polymer matrix or gel.

In certain embodiments, after application of the topical formulation to the epidermis, the area may be covered with a dressing. The term "dressing", as used herein, means a covering designed to protect a topically applied drug formulation. "Dressing" includes coverings such as a bandage, which may be porous or non-porous and various inert coverings, e.g., a plastic film wrap or other non-absorbent film. The term "dressing" also encompasses non-woven or woven coverings, particularly elastomeric coverings, which allow for heat and vapor transport. These dressings allow for cooling of the treated area, which provides for greater comfort.

In certain exemplary embodiments, pharmaceutically acceptable topical formulations of the invention are contained in a patch that is applied adjacent to the area of skin to be treated. As used herein a "patch" comprises at least a topical formulation and a covering layer, such that, the patch can be placed over the area of skin to be treated. Preferably, but not necessarily, the patch is designed to maximize drug delivery through the stratum corneum and into the epidermis or dermis, reduce lag time, promote uniform absorption, and/or reduce mechanical rub-off. In certain embodiments, when the intended use comprises the treatment of a skin condition (e.g., psoriasis), the patch is designed to minimize absorption into the circulatory system. Preferably, the patch components resemble the viscoelastic properties of the skin and conform to the skin during movement to prevent undue shear and delamination. Advantages of a patch comprising the topical formulation of the invention over conventional methods of administration include (i) that the dose is controlled by the patch's surface area, (ii) constant rate of administration, (iii) longer duration of action (the ability to adhere to the skin for 1, 3, 7 days or longer), (iv) improved patient compliance, (v) non-invasive dosing, and (vi) reversible action (i.e., the patch can simply be removed).

In certain embodiments, a patch suitable for use with the invention contains at least: (1) a backing layer and (2) a carrier formulated with a compound of the invention. Examples of patch systems suitable for practicing the invention include, but are not limited to, matrix-type patches; reservoir-type patches; multi-laminate drug-in-adhesive-type patches; and monolithic drug-in-adhesive type-patch. See, for example Ghosh, T. K.; Pfister, W. R.; Yum, S. I. Transdermal and Topical Drug Delivery Systems, Interpharm Press, Inc. p. 249-297, which is incorporated herein by reference in its entirety. These patches are well known in the art and generally available commercially.

The matrix patch comprises matrix containing an inventive compound, an adhesive backing film overlay, and preferably, but not necessarily, a release liner. In some cases, it may be necessary to include a impermeable layer to minimize drug migration into the backing film (e.g., U.S. Pat. No. 4,336,243, incorporated herein by reference). In certain embodiments, the matrix containing the inventive compound is held against the skin by the adhesive overlay. Examples of suitable matrix materials include but are not limited to lipophilic polymers, such as polyvinyl chloride, polydimethylsiloxane, and hydrophilic polymers like polyvinylpyrrolidone, polyvinyl alcohol, hydrogels based on gelatin, or polyvinylpyrrolidone/polyethylene oxide mixtures. Suitable release liners include but are not limited to occlusive, opaque, or clear polyester films with a thin coating of pressure sensitive release liner (e.g., silicone-fluorosilicone, and perfluorocarbon based polymers.

It will also be appreciated that the compounds and pharmaceutical compositions of the present invention can be formulated and employed in combination therapies, that is, the compounds and pharmaceutical compositions can be formulated with or administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another immunomodulatory agent, anticancer agent or agent useful for the treatment of psoriasis), or they may achieve different effects (e.g., control of any adverse effects).

For example, other therapies or anticancer agents that may be used in combination with the inventive compounds of the present invention include surgery, radiotherapy (in but a few examples, γ-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), to name a few. For a more comprehensive discussion of updated cancer therapies see, The Merck Manual, Seventeenth Ed. 1999, the entire contents of which are hereby incorporated by reference. See also the National Cancer Institute (CNI) website (www.nci.nih.gov) and the Food and Drug Administration (FDA) website for a list of the FDA approved oncolsogy drugs (www.fda.gov/cder/cancer/druglistframe-See Appendix A).

In certain embodiments, the pharmaceutical compositions of the present invention further comprise one or more additional therapeutically active ingredients (e.g., chemotherapeutic and/or palliative). For purposes of the invention, the term "palliative" refers to treatment that is focused on the relief of symptoms of a disease and/or side effects of a therapeutic regimen, but is not curative. For example, palliative treatment encompasses painkillers, antinausea medications and anti-sickness drugs. In addition, chemotherapy, radiotherapy and surgery can all be used palliatively (that is, to reduce symptoms without going for cure; e.g., for shrinking tumors and reducing pressure, bleeding, pain and other symptoms of cancer).

In certain embodiments, compounds of the invention are useful for the treatment of psoriasis and pharmaceutical compositions containing them may be administered in combination with any of the antipsoriatic therapies or therapeutic agents known in the art. For example, therapies or antipsoriatic agents that may be used in combination with the inventive compounds of the present invention include Ultraviolet light treatment (e.g., sunlight), lubricants, keratolytics, emollients (e.g., Aqueous Cream, E45, and Emulsifying ointment), ammoniated mercury, topical vitamin D analogs (e.g., Calcipotriol (Dovonex), Tacalcitol (Curatoderm)), dithranol (e.g., Dithrocream and Miconal), tar (e.g., Alphosyl, anthralin), topical steroids (e.g., corticosteroids, halobetasol), topical retinoids (e.g., zorac, Tazarotene), systemic antimetabolites (e.g., oral methotrexate), immunosuppressive drugs (e.g., oral cyclosporine, tacrolimus, mycophenolate, and mofetil) and oral retinoids (e.g., acitretin).

6. EXAMPLES

The following Examples further illustrate the disclosure and are not intended to limit the scope. In particular, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims. Various modifications of the invention and many further embodiments thereof, in addition to those shown and described herein, will become apparent to those skilled in the art from the full contents of this document, including the examples which follow and the references to the scientific and patent literature cited herein. It should further be appreciated that the contents of those cited references are incorporated herein by reference to help illustrate the state of the art.

The compounds of this invention and their preparation can be understood further by the examples that illustrate some of the processes by which these compounds are prepared or used. It will be appreciated, however, that these examples do not limit the invention. Variations of the invention, now known or further developed, are considered to fall within the scope of the present invention as described herein and as hereinafter claimed. For example, the methods of U.S. Pat. No. 7,915,306; S. Brase et al., The Chemistry of Mycotoxins, Progress in the Chemistry of Organic Natural Products, Vol. 97, Chapter 9 "Resorcylic Acid Lactones" (2013); or Xu et al., "Recent progress regarding the bioactivities, biosynthesis and synthesis of naturally occurring resorcinolic macrolides," *Acta Pharmacologica Sinica*, (2014) 35:316-330 may be incorporated into methods of preparing the compounds of this invention.

The practitioner has a well-established literature of macrolide chemistry to draw upon, in combination with the information contained herein, for guidance on semi-synthetic and synthetic strategies, protecting groups, and other materials and methods useful for the synthesis or semi-synthesis of the compounds of this invention.

Moreover, the practitioner is directed to the specific guidance and examples provided in this document relating to various exemplary compounds. The compounds of this invention and their preparation can be understood further by the examples that illustrate some of the processes by which these compounds are prepared or used. It will be appreciated, however, that these examples do not limit the invention.

According to the present invention, any available techniques can be used to make or prepare the inventive compounds or compositions including them. For example, a variety of solution phase synthetic methods may be used. Alternatively or additionally, the inventive compounds may be prepared using any of a variety combinatorial techniques, parallel synthesis and/or solid phase synthetic methods known in the art.

It will be appreciated as described below, that a variety of inventive compounds can be synthesized according to the methods described herein. The starting materials and reagents used in preparing these compounds are either available from commercial suppliers such as Aldrich Chemical Company (Milwaukee, Wis.), Bachem (Torrance, Calif.), Sigma (St. Louis, Mo.), or are prepared by methods well known to a person of ordinary skill in the art following procedures described in such references as Fieser and Fieser 1991, "Reagents for Organic Synthesis", vols 1-17, John Wiley and Sons, New York, N.Y., 1991; Rodd 1989 "Chemistry of Carbon Compounds", vols. 1-5 and supps, Elsevier Science Publishers, 1989; "Organic Reactions", vols 1-40, John Wiley and Sons, New York, N.Y., 1991; March 2001, "Advanced Organic Chemistry", 5th ed. John Wiley and Sons, New York, N.Y.; and Larock 1990, "Comprehensive Organic Transformations: A Guide to Functional Group Preparations", $2^{nd}$ ed. VCH Publishers. These schemes are merely illustrative of some methods by which the compounds of this invention can be synthesized, and various modifications to these schemes can be made and will be suggested to a person of ordinary skill in the art having regard to this disclosure.

The starting materials, intermediates, and compounds of this invention may be isolated and purified using conventional techniques, including filtration, distillation, crystallization, chromatography, and the like. They may be characterized using conventional methods, including physical constants and spectral data.

I. General Experimental Procedures

Unless otherwise stated, all reactions were carried out under an atmosphere of dry nitrogen in dried glassware. Indicated reaction temperatures refer to those of the reaction bath, while room temperature (rt) is noted as 25° C. All solvents and reagents were obtained from commercial sources and were used as received. Analytical thin layer chromatography (TLC) was performed on silica gel 60 F254 precoated plates (0.25 mm) from Merck. Visualization was accomplished by irradiation under a 254 nm UV lamp. Silicycle silica gel 230-400 (particle size 40-63 m) mesh was used for all flash column chromatography. The crude extract and reaction products were purified by reverse phase chromatography, which was performed using a Varian purification system employing a Phenomenex Gemini-NX, (5 μm, C18, 110A, AX. 250×21.20 mm). The mobile phase was a mixture of acetonitrile and H2O containing 0.1% formic acid. 1H NMR spectra were recorded on a Jeol ECA 500 MHz spectrometer or a Jeol ECS 400 MHz spectrometer in the solvent indicated. All 1H NMR experiments are reported in 6 units, parts per million (ppm) downfield of TMS, and were measured relative to the signals for chloroform (7.26 ppm), methanol (3.31 ppm), acetone (2.05 ppm) and dimethylsulfoxide (2.50 ppm). All 13C NMR spectra were reported in ppm relative to the signals for chloroform (77 ppm), methanol (49 ppm), acetone (29.8 ppm) and dimethylsulfoxide (39.5 ppm) with 1H decoupled observation. Data for 1H NMR are reported as follows: chemical shift (6 ppm), multiplicity (s=singlet, d=doublet, t=triplet, q=quartet, quint=quintet, sext=sextet, sept=septet, m=multiplet), integration and coupling constant (Hz), whereas 13C NMR analyses were reported in terms of chemical shift. High resolution mass spectra (HRMS) were performed on a Thermo Fisher Scientific UPLC/LTQ Orbitrap XL system.

II. Isolation of (5Z)-7-Oxozeaenol and Related Analogues

The lead compound in this study, (5Z)-7-oxozeaenol (1), was isolated from solid-phase cultures of Nigerean leaf litter (MSX 63935) grown by Mycosynthetix, Inc™. MSX 63935 is a filamentous fungus that is a super-producer of (5Z)-7-oxozeaenol. It reproducibly provided copious quantities exceeding 800 mg per a single solid-based culture grown in a 2.8 Fernbach flask.[15]

800 mg of the crude extract was dissolved in 2 mL of DMSO and purified via 10 separate injections by preparative HPLC using a gradient that initiated with 35:65 ($CH_3CN$/$H_2O$) and increased linearly to 45:55 over 40 min. (5Z)-7-oxozeaenol (1) and LL-Z164-1 eluted together from 16 to 20 min. The isolated mixture of 1 and LL-Z164-1 was subjected to an additional round of preparative HPLC purification under the same conditions to yield 206 mg (26%) of pure (>97%) (5Z)-7-oxozeaenol (1).

The gummy extract contained six structurally-related secondary metabolites which were purified using preparative HPLC. Two of these isolated metabolites were a Michael acceptor, namely; (5Z)-7-oxozeaenol (1) and (5E)-7-oxozeaenol (2).

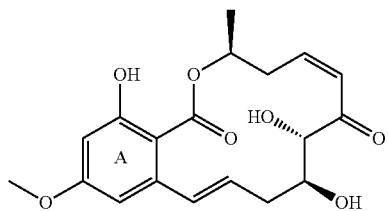

1

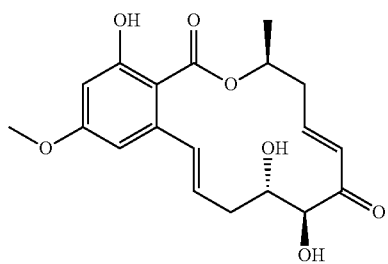

2

The cis-enone (5Z)-7-oxozeaenol (1) has greater potency in inhibiting NF-κB than the trans-enone (5E)-7-oxozeaenol (2) (11 nM versus 1.3 μM). The relative amount of cis-enone (5Z)-7-oxozeaenol (1) was much higher in the crude extract compared to trans-enone (5E)-7-oxozeaenol (2).[15]

Analogues of (5Z)-7-oxozeaenol were concomitantly isolated from this fungus and other strains and analyzed for their activities. Analogues were also synthesized using (5Z)-7-oxozeaenol as the starting material. The analogues include:

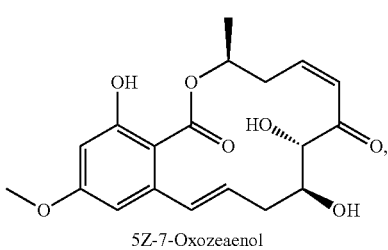

1
5Z-7-Oxozeaenol

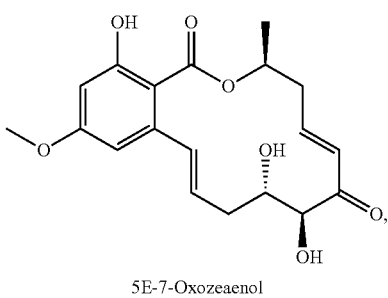

2
5E-7-Oxozeaenol

-continued

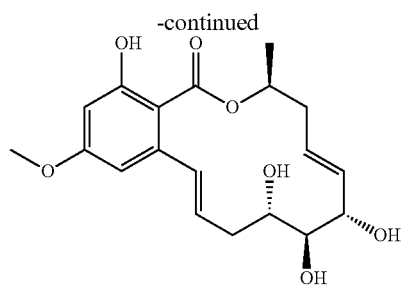

Zeaenol

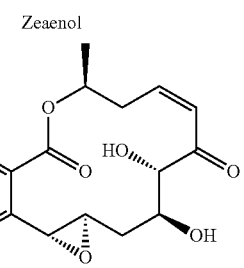

Hypothemycin

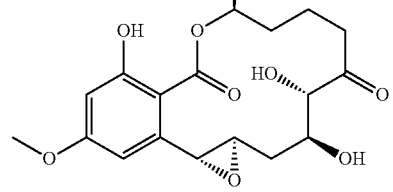

Dihydrohypothemycin

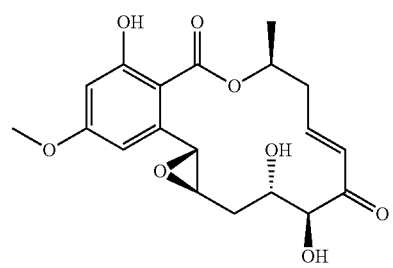

Aigialomycin A

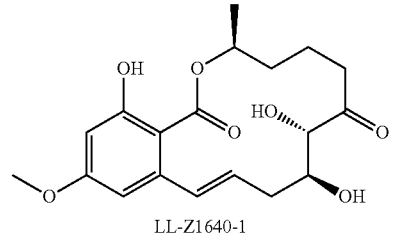

LL-Z1640-1

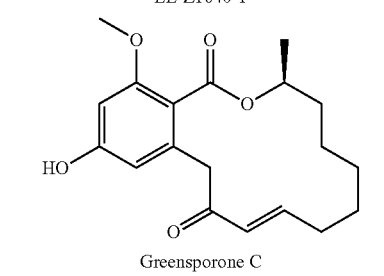

Greensporone C

III. Synthesis of Additional (5Z)-7-Oxozeaenol Analogues

The cis-enone ((5Z)-7-oxozeaenol (1)) is sensitive to both acidic and basic conditions. These conditions, in any reaction, resulted in isomerization, elimination, or intramolecular cyclization products.

Methyl 2-((1E,4S,5S,7Z,9Z)-4,5-dihydroxy-6-oxoundeca-1,7,9-trien-1-yl)-6-hydroxy-4-methoxybenzoate[18] (3) Potassium carbonate (38.1 mg, 0.28 mmol) was added to a solution of (5Z)-7-oxozeaenol (50 mg, 0.14 mmol) in DMF (2 mL) and stirred for an hour. Iodomethane (10 µL, 0.16 mmol) was then added and the mixture stirred for 4 hours. It was diluted with water (20 mL) and acidified with 1M HCl, until a pH of 2, followed by extraction with $CHCl_3$ (20 mL×3). The combined organic layers were dried using anhydrous sodium sulfate and the solvent evaporated. The residue was purified by preparative HPLC using a Phenomenex Gemini-NX column C18 (250×21.20 mm, 110 A, 5 µm spherical particle size). The column was perfused at a flow rate of 21.24 mL/min with 70% of (water, 0.1% FA) and 30% of ($CH_3CN$) over 80 min. The compound eluted at ~70 min. Yield (13%). $^1$H NMR (500 MHz, $CDCl_3$) δ 11.5 (s, 1H; 17-OH), 7.43 (ddd, J=11.5, 14.9, 17.8 Hz, 1H; 4-H), 6.98 (dd, J=15 Hz, 1H; 12-H), 6.57 (dd, J=12.0, 11.5 Hz, 1H; 5-H), 6.38 (s, 1H; 16-H), 6.26 (dd, J=14.9, 6.9 Hz, 1H; 3-H), 6.40 (s, 1H; 14-H), 6.08 (dd, J=11.5, 1.2 Hz, 1H; 6-H), 5.85 (m, 1H; 11-H), 4.36 (s, 1H; 8-H), 3.94 (m, 1H; 9-H), 3.9 (s, 3H; 21-H), 3.8 (s, 3H; 20-H), 2.36 (m, 2H; 10-H), 1.9 (d, J=6.9, 3H; 19-H). $^{13}$C NMR (125 MHz, $CDCl_3$) δ 198.9, 171.5, 164.9, 164.2, 146.7, 145.2, 142.8, 135.2, 129.3, 127.5, 117.9, 108.0, 103.0, 100.0, 79.4, 72.2, 55.5, 52.3, 35.7, 19.0. HRMS: m/z calculated for $C_{20}H_{25}O_7$ $[M+H]^+$ 376.1522; found 390.17.

Methyl 2-((1E,4S,5S,7Z,9Z)-4,5-dihydroxy-6-oxoundeca-1,7,9-trien-1-yl)-4,6-dimethoxybenzoate[18] (4) Same as procedure described for synthesis of compound 3. The compound eluted at ~46 min. UPLC was used to evaluate the purity using a gradient solvent system that initiated with 20:80 $CH_3CN$—$H_2O$ to 100% $CH_3CN$ over 4.5 min; it was >97% pure. Yield (34%). $^1$H NMR (500 MHz, $CDCl_3$) δ 7.43 (dd, J=12.6 Hz, 1H; 4-H), 6.57 (dd, J=11.5 Hz, 1H; 5-H), 6.54 (d, J=2.3 Hz, 1H; 14-H), 6.40 (d, J=16.0 Hz, 1H; 12-H), 6.34 (d, J=2.3 Hz, 1H; 16-H), 6.24 (dq, J=14.9, 6.9 Hz, 1H; 3-H), 6.13 (dt, J=15.5, 7.5 Hz, 1H; 11-H), 6.04 (d, J=11.5 Hz, 1H; 6-H), 4.35 (d, J=4.0 Hz, 1H; 8-H), 3.9 (s, 3H; 9-H), 3.86 (s, 3H; 21-H), 3.8 (s, 3H; 22-H), 3.76 (d, J=6.9 Hz, 3H; 20-H), 2.38 (m, 1H; 10-H), 2.26 (m, 1H; 10-H), 1.89 (d, J=6.9 Hz, 3H; 19-H). $^{13}$C NMR (125 MHz, $CDCl_3$) δ 198.8, 168.7, 161.5, 158.2, 146.9, 145.2, 137.8, 130.4, 129.4, 129.3, 117.9, 115.3, 101.8, 97.9, 79.4, 72.4, 56.0, 55.5, 52.5, 35.9, 19.1. HRMS: m/z calculated for $C_{21}H_{27}O_7$ $[M+H]^+$ 391.1522; found 391.1679.

Synthesis of analogues (3) and (4) as shown below, a) NaH, DMF, $CH_3I$ or $TMSCHN_2$, MeOH, r.t. b) $K_2CO_3$, DMF, $CH_3I$ or $Bu_4NOH$, DMF, $CH_3I$, r.t.:

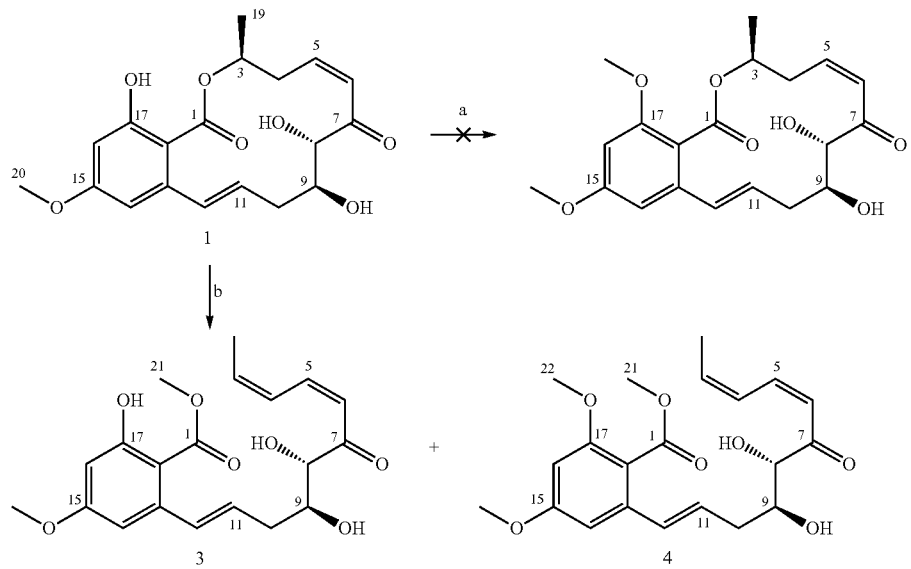

(3S,5Z,8S,9S,11E)-13,13-Difluoro-8,9-dihydroxy-14-methoxy-3-methyl-3,4,9,10-tetrahydro-1H benzo[c][1]oxacyclotetradecine-1,7,16(8H,13H)-trione2[1](5) Selectfluor® (177 mg, 0.50 mmol) was added to a solution of (5Z)-7-oxozeaenol (1) (30 mg, 0.083 mmol) in $CH_3CN$ (3 mL) and the mixture stirred for 3 hrs. The solvent was evaporated and the residue was purified by preparative HPLC using a Phenomenex Gemini-NX column C18 (250×21.20 mm, 110 A, 5 m spherical particle size). The column was perfused at a flow rate of 21.24 mL/min with 60% (water, 0.1% TFA), and 40% of (MeOH) over 40 min. UPLC was used to evaluate the purity using a gradient solvent system that initiated with 20:80 $CH_3CN$—$H_2O$ to 100% $CH_3CN$ over 4.5 min; it was >97% pure based on the ELSD detector. Yield (14%). $^1$H NMR (500 MHz, $CDCl_3$) δ 6.63 (dt, J=11.5, 4 Hz, 1H; 5H), 6.35 (ddt, J=15.5, 8.6, 7.5 Hz; 11-H), 6.31 (d, J=11.5 Hz, 1H; 6-H), 6.05 (d, J=15.5 Hz, 1H; 12-H), 5.58 (t, 2.3 Hz, 1H; 16-H), 5.43 (ddq, J=17.2, 6.3, 1.7, 1H; 3-H), 4.48 (bs, 1H; 8-H), 4.11 (m, 1H; 9-H), 3.85 (s, 3H; 20-H), 3.8 (m, 1H; 3-H), 2.57 (ddd, J=14.9, 8.0, 6.9, 1H; 10-H), 2.46 (d, 16.0 Hz, 1H; 4-H), 2.37 (dd, J=15.5, 5.2 Hz, 1H; 10-H), 1.41 (d, J=6.3 Hz, 3H; 19-H). $^{13}$C NMR (125 MHz, $CDCl_3$) δ 198.3, 181.4, 164.2, 163 (t, J=24 Hz, IC; 15-C), 150.4140.2, 138.2 (t, J=25.2 Hz, IC; 13-C), 130.8, 123.1, 122.7, 108.9, 102.3, 80.7, 73.8, 72.6, 57.0, 38.1, 37.2, 21.4). HRMS: m/z calculated for $C_{19}H_{21}F_2O_6$ [M+H]$^+$ 399.11771; found 399.124.

Synthesis of analogue (5) as shown below, a) 6 eq. Selectfluor®, $CH_3CN$:

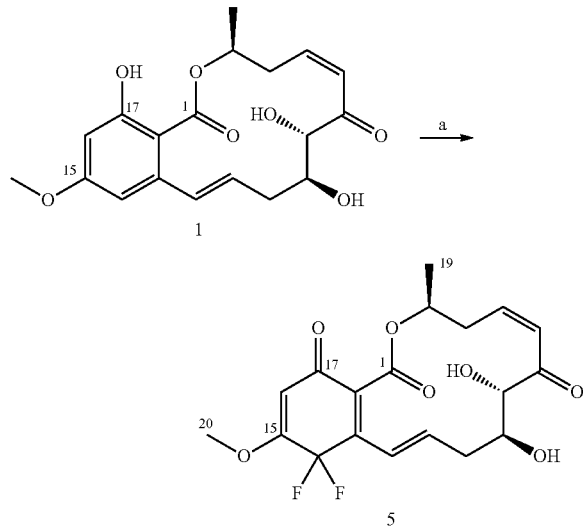

Surprisingly, the product obtained was a result of difluorination at carbon 14. Attempts to synthesize the monofluorinated compound led only to smaller amounts of the difluorinated product.

(3S,5Z,8S,9S,11E)-15-Bromo-8,9,16-trihydroxy-14-methoxy-3-methyl-3,4,9,10-tetrahydro-1H-benzo[c][1]oxacyclotetradecine-1,7(8H)-dione (6) N-Bromosuccinimide (125 mg, 0.98 mmol) was added to a solution of (5Z)-7-oxozeaenol (50 mg, 0.14 mmol) in $CHCl_3$ (2 mL) and the mixture stirred for 4 hours. The solvent was evaporated and the residue was diluted with $CHCl_3$ (5 mL) and washed with water (5 mL). The organic layer was dried and the solvent evaporated. The residue was purified by preparative HPLC using a Phenomenex Gemini-NX column C18 (250×21.20 mm, 110 A, 5 m spherical particle size). The column was perfused at a flow rate of 21.24 mL/min with a linear gradient from 50% ($CH_3CN$—$H_2O$) to 60% over 15 min. The compound eluted at 15.5 min. UPLC was used to evaluate the purity using a gradient solvent system that initiated with 20:80 $CH_3CN$—$H_2O$ to 100% $CH_3CN$ over 4.5 min; it was >97% pure. Yield (5%). $^1$H NMR (500 MHz, $CDCl_3$) δ 12.79 (s, 1H; 17-OH), 6.88 (d, J=15.3 Hz, 1H; 12-H), 6.42 (s, 1H; 14-H), 6.34 (dd, J=11.5, 3 Hz, 1H; 6-H), 6.22 (dt, J=11.5, 3 Hz, 1H; 5-H), 6.03 (ddd, J=15.3, 10.7, 4.6 Hz, 1H; 11-H), 5.26 (dq, Jd=8.5, Jq=6.1 Hz, 1H; 3-H), 4.53 (dd, J=5.4, 2.3 Hz, 1H; 8-H), 4.00 (bs, 1H; 9-H), 3.95 (s, 3H; 20-H), 3.57 (ddd, J=11.5, 10.7, 5.4 Hz, 1H; 4-H), 2.53 (dd, J=17.6, 2.3 Hz, 1H; 4-H), 2.23-2.11 (m, 2H; 10-H), 1.48 (d, J=6.1 Hz, 3H; 19-H). $^{13}$C NMR (100 MHz, $CDCl_3$) δ 199.0, 171.1, 161.4, 160.4, 147.6, 142.3, 132.9, 131.1, 125.3, 104.8, 103.7, 99.1, 80.9, 74.6, 73.6, 56.5, 37.5, 37.1, 20.8. HRMS (ESI, m/z): Calculated for $C_{19}H_{22}^{79}BrO_7$ [M+H]$^+$ 441.0543; found 441.0546 (0.6 ppm), Calculated for $C_{19}H_{22}^{81}BrO_7$ [M+H]$^+$ 443.0523; found 443.0521 (0.4 ppm).

(3S,5Z,8S,9S,11E)-13-Bromo-8,9,16-trihydroxy-14-methoxy-3-methyl-3,4,9,10-tetrahydro-1H-benzo[c][1]oxacyclotetradecine-1,7(8H)-dione (7) Same as procedure described for synthesis of compound 6. The compound eluted at 22 min. UPLC was used to evaluate the purity using a gradient solvent system that initiated with 20:80 $CH_3CN$—$H_2O$ to 100% $CH_3CN$ over 4.5 min; it was >97% pure. Yield (5%). $^1$H NMR (500 MHz, $CDCl_3$) δ 12.12 (s, 1H; 17-OH), 6.43 (s, 1H; 16-H), 6.39 (dd, J=15.3, 2 Hz, 1H; 12-H), 6.31 (dd, J=11.5, 2.9 Hz, 1H; 6-H), 6.18 (ddd, J=11.5, 10.9, 2.9 Hz, 1H; 5-H), 5.72 (ddd, J=16.0, 10.3, 3.2 Hz, 1H; 11-H), 5.40 (dq, Jd=8.5, Jq=6.1 Hz, 1H; 3-H), 4.55 (bs, 1H; 8-H), 3.95 (bs, 1H; 9-H), 3.89 (s, 3H; 20-H), 3.74 (d, J=4.0 Hz, 1H; 8-OH), 3.35 (ddd, J=11.5, 10.9, 5.4 Hz, 1H; 4-H), 2.51 (dd, J=17.2, 2.3 Hz, 1H; 4-H), 2.33 (dd, J=16.6, 2.3 Hz, 1H; 10-H), 2.10 (ddd, J=16.6, 10.3, 2.9 Hz, 1H; 10-H), 1.46 (d, J=6.1 Hz, 3H; 19-H). $^{13}$C NMR (125 MHz, $CDCl_3$) δ 199.4, 170.9, 164.4, 161.1, 146.6, 142.2, 133.9, 129.6, 125.6, 105.8, 105.4, 99.5, 81.0, 73.8, 73.1, 56.7, 37.0, 36.8, 21.0. HRMS (ESI, m/z): Calculated for $C_{19}H_{22}^{79}BrO_7$ [M+H]$^+$ 441.0543; found 441.0546 (0.6 ppm), Calculated for $C_{19}H_{22}^{81}BrO_7$ [M+H]$^+$ 443.0523; found 443.0522 (0.2 ppm).

(3S,5Z,8S,9S,11E)-13,15-Dibromo-8,9,16-trihydroxy-14methoxy-3-methyl-3,4,9,10-tetrahydro-1H-benzo[c][1]oxacyclotetradecine-1,7(8H)-dione (8) Same as procedure described for synthesis of compound 6. The compound eluted at 28.5 min. UPLC was used to evaluate the purity using a gradient solvent system that initiated with 20:80 $CH_3CN$—$H_2O$ to 100% $CH_3CN$ over 4.5 min; it was >97% pure. Yield (5%). $^1$H NMR (500 MHz, $CDCl_3$) δ 12.46 (s, 1H; 17-OH), 6.37 (d, J=16.0 Hz, 1H; 12-H), 6.32 (dd, J=11.5, 2.9 Hz, 1H; 6-H), 6.20 (ddd, J=11.5, 10.9, 2.9 Hz, 1H; 5-H), 5.72 (ddd, J=16.0, 10.3, 3.4 Hz, 1H; 11-H), 5.47 (dq, Jd=11.5, 6.3 Hz, 1H; 3-H), 4.55 (dd, J=5.2, 2.3, 1H; 8-H), 4.55 (dd, J=5.2, 2.3 Hz, 1H; 8-H), 3.95 (bs, 1H; 9-H), 3.90 (s, 3H; 20-H), 3.72 (d, J=5.2 Hz, 1H; 8-OH), 3.40 (ddd, J=11.5, 11.2, 10.9 Hz, 1H; 4-H), 2.53 (ddd, J=17.5, 2.9, 2.3 Hz, 1H; 4-H), 2.33 (m, H; 10-H), 2.13 (ddd, J=16.6, 10.3, 2.3 Hz, 1H; 10-H), 1.39 (d, J=6.3 Hz, 3H; 19-H). $^{13}$C NMR (100 MHz, $CDCl_3$) δ 199.2, 170.5, 160.0, 159.6, 146.4, 141.3, 134.6, 129.1, 125.1, 104.7, 103.6, 99.0, 80.9, 74.8, 73.0, 60.6, 37.0, 36.8, 21. HRMS (ESI, m/z): Calculated for $C_{19}H_{21}^{79}Br_2O_7$ [M+H]$^+$ 518.9648; found 518.9633 (3.0 ppm), Calculated for $C_{19}H_{21}^{79}Br^{81}BrO_7$ [M+H]$^+$ 520.9628; found 520.9613 (2.9 ppm), Calculated for $C_{19}H_{21}^{81}Br_2O_7$ [M+H]$^+$ 522.9608; found 522.9593 (2.8 ppm).

Synthesis of analogue (6)-(8) as shown below, a) $Cu(OTf)_2$, $H_2O_2$, $NaO_2SCF_3$; b) NBS, $CHCl_3$.

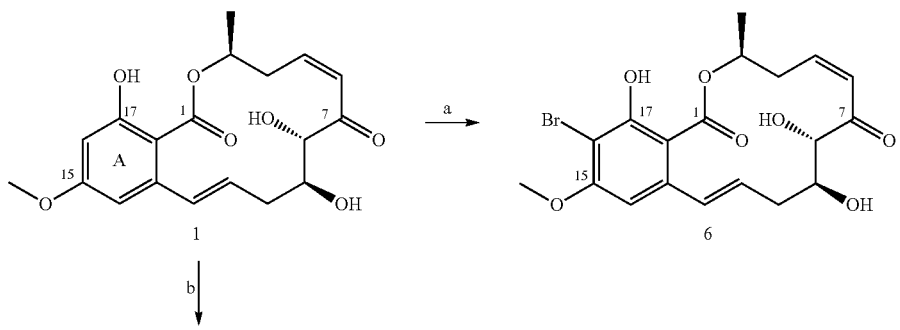

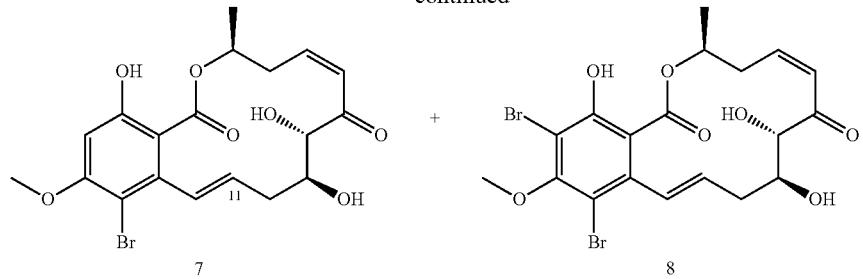

Unexpectedly, the major product obtained when using sodium trifluoromethane sulfinate, copper (II) trifluoromethane sulfonate and hydrogen peroxide[22] resulted in the formation of bromide (6). It is surmised that the trace impurities of a bromine-containing contaminant, as suggested by mass analysis of sodium trifluoromethane sulfinate, was the source of reactive bromine. Interestingly, when arene ((5Z)-7-oxozeaenol (1)) was treated with NBS, bromination at the other position, or at both positions occurred.[23]

(1[2]S,1[3]S,8S,E)-1[3],5[3]-Dihydroxy-5[5]-methoxy-8-methyl-1[3],1[4],1[5],1[6]-tetrahydro-1[2]H-7-oxa-1(2,6)-pyrana-5(1,2)benzenacyclononaphan-3-ene-1[4],6-dione[25] (9) p-Toluenesulfonic acid (15 mg, 0.082 mmol) were added to a solution of (5Z)-7-oxozeaenol in $CH_2Cl_2$ (2 mL) and the mixture stirred overnight. It was extracted with 10% $NaHCO_3$(2 mL), the organic layer dried and the solvent evaporated. The residue was purified by preparative HPLC using a Phenomenex Gemini-NX column C18 (250×21.20 mm, 110 A, 5 m spherical particle size). The column was perfused at a flow rate of 21.24 mL/min with solvent A (water, 0.1% TFA), and a linear gradient from 40% to 50% of solvent B ($CH_3CN$) over 30 min. UPLC was used to evaluate the purity using a gradient solvent system that initiated with 20:80 $CH_3CN$—$H_2O$ to 100% $CH_3CN$ over 4.5 min; it was >97% pure. Yield (35%). $^1$H NMR (500 MHz, $CDCl_3$) δ 11.19 (s, 1H; 17-OH), 7.12 (d, J=16.0 Hz, 1H; 12-H), 6.36 (d, J=2.8 Hz, 1H; 16-H), 6.33 (d, 2.8 Hz, 1H; 14-H), 5.83 (dt, J=6.9, 6.4 Hz, 1H; 11-H), 5.16 (m, 1H; 3-H), 4.65 (m, 1H; 5-H), 4.12 (m, 1H; 8-H), 3.85 (m, 1H; 9-H), 3.80 (s, 3H; 20-H), 3.54 (d, J=4.1 Hz, 1H; 8-OH), 2.89 (dd, J=15.1, 6.9 Hz, 1H; 6-H), 2.72 (dd, J=15.1, 6.9, 1H; 10-H), 2.48 (dd, 15.1, 3.66 Hz, 1H; 6-OH), 2.41 (m, 1H; 10-H), 2.20 (m, 1H; 4-H), 1.54 (m, 1H; 4-H). $^{13}$C NMR (125 MHz, $CDCl_3$) δ 207.6, 171.0, 164.2, 164, 143.6, 135.5, 125.6, 107.4, 105.0, 99.6, 77.5, 76.1, 73.1, 72.3, 55.4, 46.1, 37.1, 33.2, 21.6. HRMS: m/z calculated for $C_{19}H_{23}O_7$ [M+H]$^+$ 363.13655; found 363.1433.

(3aS,5Z,8S,15E,17aS)-11-Hydroxy-13-methoxy-2,2,8-trimethyl-7,8,17,17a-tetrahydro-4H-benzo[c][1,3]dioxolo[4,5-h][1]oxacyclotetradecine-4,10(3aH)-dione[1] (10) Few crystals of p-toluenesulfonic acid were added to a suspension of (5Z)-7- oxozeaenol (47 mg, 0.13 mmol) in dimethoxypropane (20 mL) and the mixture stirred for an hour. Dimethoxypropane was evaporated and the residue dissolved in $CHCl_3$ (20 mL) and extracted with 10% aqueous $NaHCO_3$(10 mL). The organic layer was dried over anhydrous magnesium sulfate and the solvent evaporated. The residue was purified by preparative HPLC using a Phenomenex Gemini-NX C18 column (250×21.20 mm, 110 A, 5 μm spherical particle size). The column was perfused at a 12-H), 6.37 (s, 2H; 14-H and 15-H), 5.70 (m, 1H; 11-H), 5.38 (bs, 1H; 3-H), 4.57 (m, 1H; 8-H), 4.57 (m, 1H; 9-H), 3.79 (s, 3H; 20-H), 2.65 (m, 2H; 10-H), 1.58 (s, 3H; 21-H), 1.45 (d, J=6.3 Hz, 3H; 19-H). 1.38 (s, 3H; 22-H). $^{13}$C NMR (125 MHz, $CDCl_3$) δ 196.5, 171.1, 165.6, 163.9, 146.3, 142.6, 133.6, 127.1, 126.6, 110.0, 108.9, 103.6, 100.1, 81.7, 77.2, 73.0, 55.4, 35.8, 27.0, 25.2, 19.9. HRMS: m/z calculated for $C_{22}H_{27}O_7$ [M+H]$^+$ 403.1679; found 403.1679.

Synthesis of analogues (9) and (10) as shown below, a) Dimethoxy propane, 0.2 eq. p-TSA. b) Dimethoxy propane, few crystals of p-TSA:

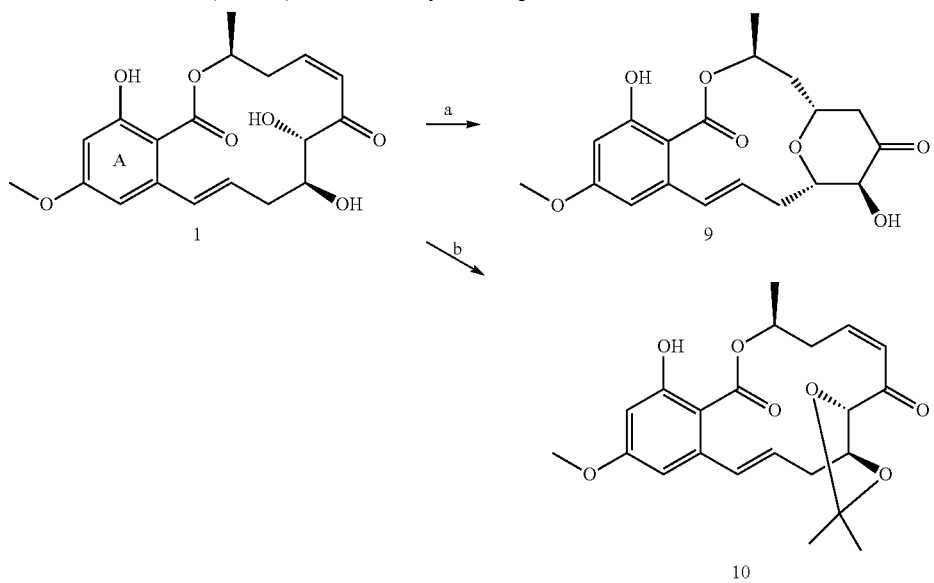

Dimethoxypropane with catalytic amounts of p-toluenesulfonic acid was successful if only few crystals[1] of the acid were used. Larger amounts than only a few crystals[25] activated the carbonyl at carbon 9 and facilitated intramolecular conjugate addition of the oxygen at carbon 9 to give pyranone (9).

IV. TaK1-TaB1 (Transforming Growth Factor-3 Activated Linase-1/TAK-1 Binding Protein 1) Inhibitor Assays The assay was performed at BSP Biosience Inc. (5Z)-7-oxozeaenol was used as a positive control. Analogue 3 was not tested due to the short-term stability as indicated by the sub 90% purity detected by UPLC following prep HPLC purification. The only synthesized analogue that was found to be relatively active was difluoro (5Z)-7-oxozeaenol 5. The potency of compound 5 indicates that the aromatic ring is not crucial for binding.

TABLE 1

$IC_{50}$ values of RAL analogues against TAK-1 enzyme

| Compound | $IC_{50}$ (μM) | 95% Confidence Intervals |
| --- | --- | --- |
| (5Z)-7-oxozeaenol | 0.011 | 0.009-0.015 |
| (5E)-7-oxozeaenol | 1.3 | 0.932-1.780 |
| zeaenol | 10 | 8.168-12.441 |
| LL-Z164-1 | 2.6 | 2.206-3.150 |
| hypothemycin | 0.033 | 0.024-0.045 |
| dihydrohypothemycin | >30 | NA |
| aigialomycin A | 0.99 | |
| 4 | >30 | NA |
| 5 | 0.077 | 0.047-0.125 |
| 6 | 2.6 | 2.206-3.150 |
| 7 | 0.36 | 0.27-0.50 |
| 8 | 8.9 | 7.7-10.5 |
| 9 | >30 | NA |
| 10 | 0.38 | 0.220-0.655 |

V. Covalent Docking

Ligand Preparation. Prior to docking, ligands having the Michael acceptor moiety, were examined using Spartan (Wavefunction, Inc.). The structures of those ligands were first subjected to conformational searches using semiempirical molecular mechanics. The resulting conformers, ranging from 100-600, were further optimized using Hartree-Fock implementing the 6-31G basis set. The theoretical global minimum energy conformation was chosen to be docked into the crystal structure.

All calculations were carried out using SPARTAN'08 for Linux. Initial conformational analyses were carried out on each ligand using a Monte-Carlo molecular mechanics conformational search using the RM1/semi-empirical force field at the ground state. All resulting conformations with $E_{rel}$ less than 10 kcal/mol, relative to the lowest-energy conformation, were then modeled using Hartree-Fock with the 6-31G* basis set in the gas phase. The resulting global minimum was exported to maestro as mol.2 file and subjected to covalent docking.

Covalent Docking. The prepared ligands were docked using the Chen et al reported crystal structure (PDB 4GS6).[12] Prior to covalent docking, the crystal structure (PDB ID: 4GS6) was prepared using protein preparation wizard, implemented in Maestro, where only hydrogens were added to all atoms and bond orders were assigned. The covalent linkage between the cocrystallized (5Z)-7-oxozeaenol TAK-1 enzyme was broken, the ligand deleted and the bare enzyme used as the binding protein for docking. Covalent docking, implemented in Glide, was used to evaluate the relative binding affinities of the various ligands tested. The reaction type chosen was Michael addition where amino acid Cysteine 174 was identified as the reactive reside. The grid box was determined as the centroid of residues Cysteine 174, valine 42 and alanine 46. Cysteine 174 was not chosen as the sole determinant of the grid box because it is impeded at the back of the binding pocket thus will not result in spanning the biding site efficiently. Many residue combinations were screened and the aforementioned collection was representative of a box holding all atoms of the co-crystallized (5Z)-7-oxozeaenol in the original crystal structure.

To validate the accuracy of the calculations performed in regards to our work, (5Z)-7-oxozeaenol was the first ligand to be docked and the output was superimposed to the crystal structure having an RMSD of 0.0984° A (FIG. 1). The configuration of the β carbon for the best-scored docking output is R. The geometry shown in the crystal structure is that of an $sp^2$ carbon. It is assumed that the geometry of carbons 5 and 6 in the crystal structure are incorrectly assigned since both of these carbons should be $sp^3$ hybridized after addition of the cysteine. It is therefore not clear which model, R or S truly fits better for the preferred ligand binding geometry.

Similar to the parent ligand, semisynthesized and isolated RALs, bearing an enone, were also docked covalently. The best docking orientations, as judged by the docking score, were further subjected to protein refinement using prime implemented in Maestro followed by covalent docking of the minimization outputs (Table 2). The scores obtained appeared to be in an acceptable alignment with the experimental data. Distinct gaps are observed between compounds having inhibitory concentrations in the nM range, M range, and the inactive compounds. Analogues having low nM inhibitory concentration had docking scores of −12 to −12.9 Kcal/mol. A range of −10 to −11.5 Kcal/mol was representative of analogues having 0.5-2.6 μrange of activities. As for inactive compounds, they had considerably higher docking scores as compared with the active compounds.

TABLE 2

Docking scores of enone-containing natural and semisynthetic RALs following prime minimization. The compounds are arranged in a descending order in regards to their inhibitory concentrations.

| Structure | Docking Score After Prime mini. | $IC_{50}$ (μM) |
| --- | --- | --- |
| (5Z)-7-oxozeaenol | −12.9 | 0.011 |
| hypothemycin | −12.0 | 0.033 |
| 5 | −12.9 | 0.077 |
| 7 | −10.2 | 0.36 |
| 10 | −10.8 | 0.38 |
| (5E)-7-oxozeaenol | −11.5 | 1.3 |
| 6 | −10.0 | 2.6 |
| 8 | −6.8 | 8.9 |
| Greensporone C | −8.4 | >30 |
| 4 | −6.4 | >30 |

The initial covalent docking output with the highest score for each docked ligand was minimized using prime, implemented in Maestro. All atoms including those of the enzyme and the ligand were minimized using VSGB solvation model. The number of iterations implemented for the automatic method of minimization was 8 and steps per iterations were 200. The covalent linkage between the docked ligand and the enzyme was broken again and the minimized ligand was covalently docked in the minimized enzyme.

7. REFERENCES

1. Ellestad, G. A.; Lovell, F. M.; Perkinson, N. A.; Hargreaves, R. T.; McGahren, W. J., New zearalenone related macrolides and isocoumarins from an unidentified fungus. *The Journal of Organic Chemistry* 1978, 43 (12), 2339-2343.
2. Ninomiya-Tsuji, J.; Kajino, T.; Ono, K.; Ohtomo, T.; Matsumoto, M.; Shiina, M.; Mihara, M.; Tsuchiya, M.; Matsumoto, K., A resorcylic acid lactone, 5Z-7-oxozeaenol, prevents inflammation by inhibiting the catalytic activity of TAK1 MAPK kinase kinase. *The Journal of biological chemistry* 2003, 278 (20), 18485-90.
3. Yamaguchi, K.; Shirakabe, K.; Shibuya, H.; Irie, K.; Oishi, I.; Ueno, N.; Taniguchi, T.; Nishida, E.; Matsumoto, K., Identification of a member of the MAPKKK family as a potential mediator of TGF-beta signal transduction. *Science (New York, N.Y.)* 1995, 270 (5244), 2008-11.
4. Schuman, J.; Chen, Y.; Podd, A.; Yu, M.; Liu, H.-H.; Wen, R.; Chen, Z. J.; Wang, D., A critical role of TAK1 in B-cell receptor-mediated nuclear factor κB activation. *Blood* 2009, 113 (19), 4566-4574.
5. Ninomiya-Tsuji, J.; Kishimoto, K.; Hiyama, A.; Inoue, J.; Cao, Z.; Matsumoto, K., The kinase TAK1 can activate the NIK-I kappaB as well as the MAP kinase cascade in the IL-1 signalling pathway. *Nature* 1999, 398 (6724), 252-6.
6. Johnson, G. L.; Dohlman, H. G.; Graves, L. M., MAPK kinase kinases (MKKKs) as a target class for small-molecule inhibition to modulate signaling networks and gene expression. *Current opinion in chemical biology* 2005, 9 (3), 325-31.
7. Singh, A.; Sweeney, M. F.; Yu, M.; Burger, A.; Greninger, P.; Benes, C.; Haber, D. A.; Settleman, J., TAK1 inhibition promotes apoptosis in KRAS-dependent colon cancers. *Cell* 2012, 148 (4), 639-50.
8. Meng, F.; Li, Y.; Tian, X.; Fu, L.; Yin, Y.; Sui, C.; Ma, P.; Jiang, Y., Identification of TGF-beta-activated kinase 1 as a possible novel target for renal cell carcinoma intervention. *Biochemical and biophysical research communications* 2014, 453 (1), 106-11.
9. Wang, Y.; Tu, Q.; Yan, W.; Xiao, D.; Zeng, Z.; Ouyang, Y.; Huang, L.; Cai, J.; Zeng, X.; Chen, Y. J.; Liu, A., CXC195 suppresses proliferation and inflammatory response in LPS-induced human hepatocellular carcinoma cells via regulating TLR4-MyD88-TAK1-mediated NF-kappaB and MAPK pathway. *Biochemical and biophysical research communications* 2014.
10. Melisi, D.; Xia, Q.; Paradiso, G.; Ling, J.; Moccia, T.; Carbone, C.; Budillon, A.; Abbruzzese, J. L.; Chiao, P. J., Modulation of pancreatic cancer chemoresistance by inhibition of TAK1. *Journal of the National Cancer Institute* 2011, 103 (15), 1190-204.
11. Zhang, J.; Yang, P. L.; Gray, N. S., Targeting cancer with small molecule kinase inhibitors. Nature reviews. *Cancer* 2009, 9 (1), 28-39.
12. Wu, J.; Powell, F.; Larsen, N. A.; Lai, Z.; Byth, K. F.; Read, J.; Gu, R. F.; Roth, M.; Toader, D.; Saeh, J. C.; Chen, H., Mechanism and in vitro pharmacology of TAK1 inhibition by (5Z)-7-Oxozeaenol. *ACS chemical biology* 2013, 8 (3), 643-50.
13. Singh, J.; Petter, R. C.; Baillie, T. A.; Whitty, A., The resurgence of covalent drugs. Nature reviews. *Drug discovery* 2011, 10 (4), 307-17.
14. Kilty, I.; Green, M. P.; Bell, A. S.; Brown, D. G.; Dodd, P. G.; Hewson, C.; Hughes, S. J.; Phillips, C.; Ryckmans, T.; Smith, R. T.; van Hoorn, W. P.; Cohen, P.; Jones, L. H., TAK1 inhibition in the DFG-out conformation. *Chemical biology & drug design* 2013, 82 (5), 500-5.
15. Ayers, S.; Graf, T. N.; Adcock, A. F.; Kroll, D. J.; Matthew, S.; Carcache de Blanco, E. J.; Shen, Q.; Swanson, S. M.; Wani, M. C.; Pearce, C. J.; Oberlies, N. H., Resorcylic Acid Lactones with Cytotoxic and NF-κB Inhibitory Activities and Their Structure-Activity Relationships. *Journal of Natural Products* 2011, 74 (5), 1126-1131.
16. Goto, M.; Chow, J.; Muramoto, K.; Chiba, K.; Yamamoto, S.; Fujita, M.; Obaishi, H.; Tai, K.; Mizui, Y.; Tanaka, I.; Young, D.; Yang, H.; Wang, Y. J.; Shirota, H.; Gusovsky, F., E6201 [(3S,4R,5Z,8S,9S,11E)-14-(ethylamino)-8, 9,16-trihydroxy-3,4-dimethyl-3,4,9,19-tetrahydro-1H-2-benzoxacyclotetradecine-1,7 (8H)-dione], a novel kinase inhibitor of mitogen-activated protein kinase/extracellular signal-regulated kinase kinase (MEK)-1 and MEK kinase-1: in vitro characterization of its anti-inflammatory and antihyperproliferative activities. *The Journal of pharmacology and experimental therapeutics* 2009, 331 (2), 485-95.
17. Wu, H.; Thatcher, L. N.; Bernard, D.; Parrish, D. A.; Deschamps, J. R.; Rice, K. C.; MacKerell, A. D.; Coop, A., Position of Coordination of the Lithium Ion Determines the Regioselectivity of Demethylations of 3,4-Dimethoxymorphinans with L-Selectride. *Organic Letters* 2005, 7 (13), 2531-2534.
18. Dean, M. A.; Hitchcock, S. R., Synthesis and application of oxadiazines as chiral ligands for the enantioselective addition of diethylzinc to aldehydes. *Tetrahedron: Asymmetry* 2010, 21 (20), 2471-2478.
19. Zea-Ponce, Y.; Mavel, S.; Assaad, T.; Kruse, S. E.; Parsons, S. M.; Emond, P.; Chalon, S.; Giboureau, N.; Kassiou, M.; Guilloteau, D., Synthesis and in vitro evaluation of new benzovesamicol analogues as potential imaging probes for the vesicular acetylcholine transporter. *Bioorganic & Medicinal Chemistry* 2005, 13 (3), 745-753.
20. Wang, J.; Sinchez-Rosell6, M.; Acefia, J. L.; del Pozo, C.; Sorochinsky, A. E.; Fustero, S.; Soloshonok, V. A.; Liu, H., Fluorine in Pharmaceutical Industry: Fluorine-Containing Drugs Introduced to the Market in the Last Decade (2001-2011). *Chemical Reviews* 2013, 114 (4), 2432-2506.
21. Woodhead, A. J.; Angove, H.; Carr, M. G.; Chessari, G.; Congreve, M.; Coyle, J. E.; Cosme, J.; Graham, B.; Day, P. J.; Downham, R.; Fazal, L.; Feltell, R.; Figueroa, E.; Frederickson, M.; Lewis, J.; McMenamin, R.; Murray, C. W.; O'Brien, M. A.; Parra, L.; Patel, S.; Phillips, T.; Rees, D. C.; Rich, S.; Smith, D.-M.; Trewartha, G.; Vinkovic, M.; Williams, B.; Woolford, A. J. A., Discovery of (2,4-Dihydroxy-5-isopropylphenyl)-[5-(4-methylpiperazin-1-ylmethyl)-1,3-dihydroisoindol-2-yl]methanone (AT13387), a Novel Inhibitor of the Molecular Chaperone Hsp90 by Fragment Based Drug Design. *Journal of medicinal chemistry* 2010, 53 (16), 5956-5969.
22. Langlois, B. R.; Laurent, E.; Roidot, N., Trifluoromethylation of aromatic compounds with sodium trifluoromethanesulfinate under oxidative conditions. *Tetrahedron Letters* 1991, 32 (51), 7525-7528.
23. Dijkstra, P. J.; Den Hertog, H. J.; Van Steen, B. J.; Zijlstra, S.; Skowronska-Ptasinska, M.; Reinhoudt, D. N.; Van Eerden, J.; Harkema, S., Use of pyrylium synthons in the synthesis of hemispherands with modified cavities.

X-ray structures of the 21-hemispherand and a pyrido hemispherand. *The Journal of Organic Chemistry* 1987, 52 (12), 2433-2442.

24. Xu, J.; Chen, A.; Go, M.-L.; Nacro, K.; Liu, B.; Chai, C. L. L., Exploring Aigialomycin D and Its Analogues as Protein Kinase Inhibitors for Cancer Targets. *ACS Medicinal Chemistry Letters* 2011, 2 (9), 662-666.

25. Schmidt, B.; Staude, L.; Kelling, A.; Schilde, U., A Cross-Metathesis-Conjugate Addition Route to Enantiopure γ-Butyrolactams and γ-Lactones from a C2-Symmetric Precursor. *European Journal of Organic Chemistry* 2011, 2011 (9), 1721-1727.

26. Bettermann, K.; Vucur, M.; Haybaeck, J.; Koppe, C.; Janssen, J.; Heymann, F.; Weber, A.; Weiskirchen, R.; Liedtke, C.; Gassler, N.; Muiller, M.; de Vos, R.; Wolf, M. J.; Boege, Y.; Seleznik, G. M.; Zeller, N.; Erny, D.; Fuchs, T.; Zoller, S.; Cairo, S.; Buendia, M.-A.; Prinz, M.; Akira, S.; Tacke, F.; Heikenwalder, M.; Trautwein, C.; Luedde, T., TAK1 Suppresses a NEMO-Dependent but NF-κB-Independent Pathway to Liver Cancer. *Cancer Cell* 2010, 17 (5), 481-496.

27. Wu, X.; Zhang, W.; Font-Burgada, J.; Palmer, T.; Hamil, A. S.; Biswas, S. K.; Poidinger, M.; Borcherding, N.; Xie, Q.; Ellies, L. G.; Lytle, N. K.; Wu, L.-W.; Fox, R. G.; Yang, J.; Dowdy, S. F.; Reya, T.; Karin, M., Ubiquitin-conjugating enzyme Ubc13 controls breast cancer metastasis through a TAK1-p38 MAP kinase cascade. *Proceedings of the National Academy of Sciences* 2014, 111 (38), 13870-13875.

28. Han, M., Autophagy inhibition can overcome radioresistance in breast cancer cells through suppression of TAK1 activation. *Anticancer Research* 2014, 34 (3), 1449.

29. Jackson-Bernitsas, D. G.; Ichikawa, H.; Takada, Y.; Myers, J. N.; Lin, X. L.; Darnay, B. G.; Chaturvedi, M. M.; Aggarwal, B. B., Evidence that TNF-TNFR1-TRADD-TRAF2-RIP-TAK1-IKK pathway mediates constitutive NF-[kappa]B activation and proliferation in human head and neck squamous cell carcinoma. *Oncogene* 2006, 26 (10), 1385-1397.

30. Giroux, V.; Iovanna, J.; Dagorn, J.-C., Probing the human kinome for kinases involved in pancreatic cancer cell survival and gemcitabine resistance. *The FASEB Journal* 2006, 20 (12), 1982-1991.

31. Makita, M.; Hiraki, A.; Azuma, T.; Tsuboi, A.; Oka, Y.; Sugiyama, H.; Fujita, S.; Tanimoto, M.; Harada, M.; Yasukawa, M., Antilung Cancer Effect of WT1-specific Cytotoxic T Lymphocytes. *Clinical Cancer Research* 2002, 8 (8), 2626-2631.

32. Kondo, M.; Osada, H.; Uchida, K.; Yanagisawa, K.; Masuda, A.; Takagi, K.; Takahashi, T.; Takahashi, T., Molecular cloning of human TAK1 and its mutational analysis in human lung cancer. *International Journal of Cancer* 1998, 75 (4), 559-563.

33. Bosman, M. C. J.; Schepers, H.; Jaques, J.; Brouwers-Vos, A. Z.; Quax, W. J.; Schuringa, J. J.; Vellenga, E., The TAK1-NF-κB axis as therapeutic target for AML. *Blood* 2014, 124 (20), 3130-3140.

34. Cai, P. C.; Shi, L.; Liu, V. W.; Tang, H. W.; Liu, I. J.; Leung, T. H.; Chan, K. K.; Yam, J. W.; Yao, K. M.; Ngan, H. Y.; Chan, D. W., Elevated TAK1 augments tumor growth and metastatic capacities of ovarian cancer cells through activation of NF-kappaB signaling. *Oncotarget* 2014, 5 (17), 7549-62.

It should be understood that the above description is only representative of illustrative embodiments and examples. For the convenience of the reader, the above description has focused on a limited number of representative examples of all possible embodiments, examples that teach the principles of the disclosure. The description has not attempted to exhaustively enumerate all possible variations or even combinations of those variations described. That alternate embodiments may not have been presented for a specific portion of the disclosure, or that further undescribed alternate embodiments may be available for a portion, is not to be considered a disclaimer of those alternate embodiments. One of ordinary skill will appreciate that many of those undescribed embodiments, involve differences in technology and materials rather than differences in the application of the principles of the disclosure. Accordingly, the disclosure is not intended to be limited to less than the scope set forth in the following claims and equivalents.

All references, articles, publications, patents, patent publications, and patent applications cited herein are incorporated by reference in their entireties for all purposes. However, mention of any reference, article, publication, patent, patent publication, and patent application cited herein is not, and should not be taken as an acknowledgment or any form of suggestion that they constitute valid prior art. It is to be understood that, while the disclosure has been described in conjunction with the detailed description, thereof, the foregoing description is intended to illustrate and not limit the scope. Other aspects, advantages, and modifications are within the scope of the claims set forth below. All publications, patents, and patent applications cited in this specification are herein incorporated by reference as if each individual publication or patent application were specifically and individually indicated to be incorporated by reference.

What is claimed:
1. A compound having the structure:

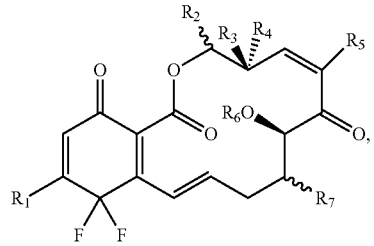

or a salt, ester, or a salt of an ester thereof; wherein $R_1$ is halogen, hydrogen, $NR_7R_8$, $OR_7$, $SR_7$, $-X_1(CH_2)_pX_2-R_9$, or is lower alkyl optionally substituted with amino, halogen, hydroxyl, hydroxyl with an oxygen protecting group, protected amino, or $-X_1(CH_2)_pX_2-R_9$;

wherein $R_7$ and $R_8$ are, independently for each occurrence, $C_2$-$C_{20}$ alkenyl, $C_1$-$C_{20}$ alkyl, $C_2$-$C_{20}$ alkynyl, $C_3$-$C_{14}$ aryl, $C_3$-$C_{20}$ cycloalkenyl, $C_3$-$C_{20}$ cycloalkyl, $C_3$-$C_{20}$ cycloalkynyl, $C_2$-$C_{20}$ heteroalkenyl, $C_1$-$C_{20}$ heteroalkyl, $C_2$-$C_{20}$ heteroalkynyl, $C_3$-$C_{14}$ heteroaryl, $C_3$-$C_{20}$ heterocycloalkenyl, $C_3$-$C_{20}$ heterocycloalkyl, $C_3$-$C_{20}$ heterocycloalkynyl, or hydrogen; or a nitrogen or oxygen protecting group, or $R_7$ and $R_8$, taken together may form a saturated or unsaturated cyclic ring of 1 to 4 carbon atoms and 1 to 3 nitrogen or oxygen atoms, and each of $R_7$ and $R_8$ are optionally further substituted with one or more alkylamino, alkyloxy, amino, aminoalkyl, halogen, hydroxyl, hydroxyl with an oxygen protecting group, or protected amino, wherein $X_1$ and $X_2$ are each independently absent, or are —N(alkyl), NH, or oxygen, or wherein $X_2$—$R_9$ together are $N_3$ or are a saturated or unsaturated heterocyclic moiety;

p is 2-10, and $R_9$ is hydrogen, or a $C_1$-$C_{20}$ alkyl($C_3$-$C_{14}$)aryl, $C_1$-$C_{20}$ alkyl($C_3$-$C_{14}$)heteroaryl, $C_3$-$C_{14}$ aryl, $C_3$-$C_{14}$ heteroaryl moiety, or is —(C=O)NHR$_{10}$, —(C=O)OR$_{10}$, or —(C=O)R$_{10}$, wherein each occurrence of $R_{10}$ is independently $C_2$-$C_{20}$ alkenyl, $C_1$-$C_{20}$ alkyl, $C_7$-$C_{20}$ alkynyl, $C_3$-$C_{14}$ aryl, $C_3$-$C_{20}$ cycloalkenyl, $C_3$-$C_{20}$ cycloalkyl, $C_3$-$C_{20}$ cycloalkynyl, $C_2$-$C_{20}$ heteroalkenyl, $C_1$-$C_{20}$ heteroalkyl, $C_2$-$C_{20}$ heteroalkynyl, $C_3$-$C_{14}$ heteroaryl, $C_3$-$C_{20}$ heterocycloalkenyl, $C_3$-$C_{20}$ heterocycloalkyl, $C_3$-$C_{20}$ heterocycloalkynyl, or hydrogen; or $R_9$ is —SO$_2$($R_{11}$), wherein $R_{11}$ is a $C_2$-$C_{20}$ alkenyl, $C_1$-$C_{20}$ alkyl, or $C_2$-$C_{20}$ alkynyl moiety, wherein one or more of $R_9$, $R_{10}$, or $R_{11}$ are optionally substituted with one or more alkylamino, alkyloxy, amino, aminoalkyl, halogen, hydroxyl, hydroxyl with an oxygen protecting group, or protected amino;

$R_2$ is $C_2$-$C_{20}$ alkenyl, $C_1$-$C_{20}$ alkyl, $C_2$-$C_{20}$ alkynyl, $C_3$-$C_{14}$ aryl, $C_3$-$C_{20}$ cycloalkenyl, $C_3$-$C_{20}$ cycloalkyl, $C_3$-$C_{20}$ cycloalkynyl, $C_2$-$C_{20}$ heteroalkenyl, $C_1$-$C_{20}$ heteroalkyl, $C_2$-$C_{20}$ heteroalkynyl, $C_3$-$C_{14}$ heteroaryl, $C_3$-$C_{20}$ heterocycloalkenyl, $C_3$-$C_{20}$ heterocycloalkyl, $C_3$-$C_{20}$ heterocycloalkynyl, or hydrogen;

$R_3$ and $R_5$ are each independently halogen or hydrogen;

$R_4$ is halogen, hydrogen, or methyl;

$R_6$ is hydrogen or an oxygen protecting group;

$R_7$ is hydrogen, hydroxyl, or hydroxyl with an oxygen protecting group;

wherein oxygen protecting groups are selected from the group consisting of acetate, benzoate, benzyl ethers, benzyloxymethyl ether, carbonates, cyclic acetals, dichloroacetate, esters, ethyl ethers, formate, ketals, methoxymethyl ether, methylthiomethyl ether, methyl ethers, p-methoxybenzyloxymethyl ether, silyl ethers, t-butyldimethylsilyl ether, t-butyldiphenyl silyl ether, tribenzyl silyl ether, triethylsilylether, trifluoroacetate, triisopropylsilyl ether, and trimethylsilyl ether and wherein nitrogen protecting groups are selected from the group consisting of amides, carbamates, cyclic imides, enamines, imines, N-alkyl amines, N-aryl amines, and Troc; and wherein $C_3$-$C_{14}$ heteroaryl moieties are selected from cyclic aromatic moieties having from five to ten ring atoms of which one ring atom is selected from N, O, and S; zero, one or two ring atoms are additional heteroatoms independently selected from N, O, and S; and the remaining ring atoms are carbon.

2. A pharmaceutical composition comprising: a pharmaceutically acceptable carrier or diluent; and a compound of claim 1.

3. The pharmaceutical composition of claim 2, wherein the compound is present in an amount effective to inhibit MAP3K.

4. The pharmaceutical composition of claim 2, wherein the compound is present in an amount effective to inhibit TAK-1.

5. A method for treating pancreatic cancer, breast cancer, or colon cancer comprising:
administering to a subject in need thereof a therapeutically effective amount of a compound of claim 1, and a pharmaceutically acceptable carrier or diluent.

* * * * *